United States Patent
Hanson et al.

(10) Patent No.: US 10,282,521 B2
(45) Date of Patent: *May 7, 2019

(54) MEDICATION MANAGEMENT AND REPORTING TECHNOLOGY

(71) Applicant: Alarm.com Incorporated, Tysons, VA (US)

(72) Inventors: Mark Andrew Hanson, Fairfax, VA (US); Elizabeth Leslie Manson, Washington, DC (US)

(73) Assignee: Alarm.com Incorporated, Tysons, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/808,688

(22) Filed: Nov. 9, 2017

(65) Prior Publication Data

US 2018/0068086 A1 Mar. 8, 2018

Related U.S. Application Data

(63) Continuation of application No. 14/754,136, filed on Jun. 29, 2015, now Pat. No. 9,842,195, which is a (Continued)

(51) Int. Cl.
*A61B 5/00* (2006.01)
*A61B 5/11* (2006.01)
(Continued)

(52) U.S. Cl.
CPC ........ *G06F 19/3456* (2013.01); *A61B 5/1113* (2013.01); *A61B 5/4833* (2013.01);
(Continued)

(58) Field of Classification Search
CPC ........ A61J 2007/049; A61J 2007/0427; G06Q 10/10; G06Q 10/1093; G06Q 50/24;
(Continued)

(56) References Cited

U.S. PATENT DOCUMENTS 5,704,366 A * 1/1998 Tacklind et al. .............. 600/529
5,827,180 A * 10/1998 Goodman ..................... 600/300
(Continued)

OTHER PUBLICATIONS

U.S. Notice of Allowance for U.S. Appl. No. 13/439,703 dated Jun. 20, 2014, 30 pages.

*Primary Examiner* — Mirza F Alam
(74) *Attorney, Agent, or Firm* — Fish & Richardson P.C.

(57) ABSTRACT

Medication management and reporting technology, in which output from at least one sensor configured to sense physical activity in a building in which medication of a patient is located is monitored and a determination is made to capture one or more images of the medication based on the monitoring. A camera is used to capture an image of the medication and the captured image is analyzed to detect a state of the medication. Information regarding a schedule by which the medication should be taken by the patient is accessed and an expected state of the medication is determined. The detected state is compared with the expected state and a determination is made that the patient has departed from the schedule based on the comparison revealing that the detected state does not match the expected state. A message indicating the departure from the schedule is sent based on the determination.

19 Claims, 17 Drawing Sheets

Related U.S. Application Data continuation of application No. 14/461,702, filed on Aug. 18, 2014, now Pat. No. 9,070,267, which is a continuation of application No. 13/439,703, filed on Apr. 4, 2012, now Pat. No. 8,810,408.

(60) Provisional application No. 61/471,355, filed on Apr. 4, 2011.

(51) Int. Cl.
*G06F 19/00* (2018.01)
*G08B 21/24* (2006.01)
*A61J 7/04* (2006.01)
*G06Q 10/10* (2012.01)
*G08B 23/00* (2006.01)
*A61G 12/00* (2006.01)
*A61J 7/00* (2006.01)

(52) U.S. Cl.
CPC ............ *A61J 7/049* (2015.05); *A61J 7/0481* (2013.01); *G06F 19/3418* (2013.01); *G06F 19/3462* (2013.01); *G06Q 10/10* (2013.01); *G08B 21/24* (2013.01); *G08B 23/00* (2013.01); *A61B 5/1128* (2013.01); *A61B 2505/07* (2013.01); *A61B 2560/0242* (2013.01); *A61G 12/00* (2013.01); *A61J 7/0069* (2013.01); *A61J 7/0418* (2015.05); *A61J 7/0427* (2015.05)

(58) Field of Classification Search
CPC . G08B 23/00; G06F 19/3456; G06F 19/3418; G06F 19/3406; G06F 19/327
See application file for complete search history.

(56) References Cited

U.S. PATENT DOCUMENTS

| | | | | |
|---|---|---|---|---|
| 6,101,478 | A * | 8/2000 | Brown | A61B 5/0002 705/2 |
| 6,277,071 | B1 * | 8/2001 | Hennessy et al. | 600/300 |
| 6,954,148 | B2 * | 10/2005 | Pulkkinen | A61B 5/1113 340/572.1 |
| 7,542,911 | B2 * | 6/2009 | Barret | G06F 19/3418 705/2 |
| 8,108,226 | B2 * | 1/2012 | Barrett | G06F 19/3418 705/2 |
| 2002/0181680 | A1 * | 12/2002 | Linder | A61B 5/0006 379/106.02 |
| 2003/0144874 | A1 | 7/2003 | Barret et al. | |
| 2004/0015132 | A1 * | 1/2004 | Brown | A61B 5/0002 604/131 |
| 2011/0170378 | A1 * | 7/2011 | Hold | G06F 19/3456 368/10 |

* cited by examiner

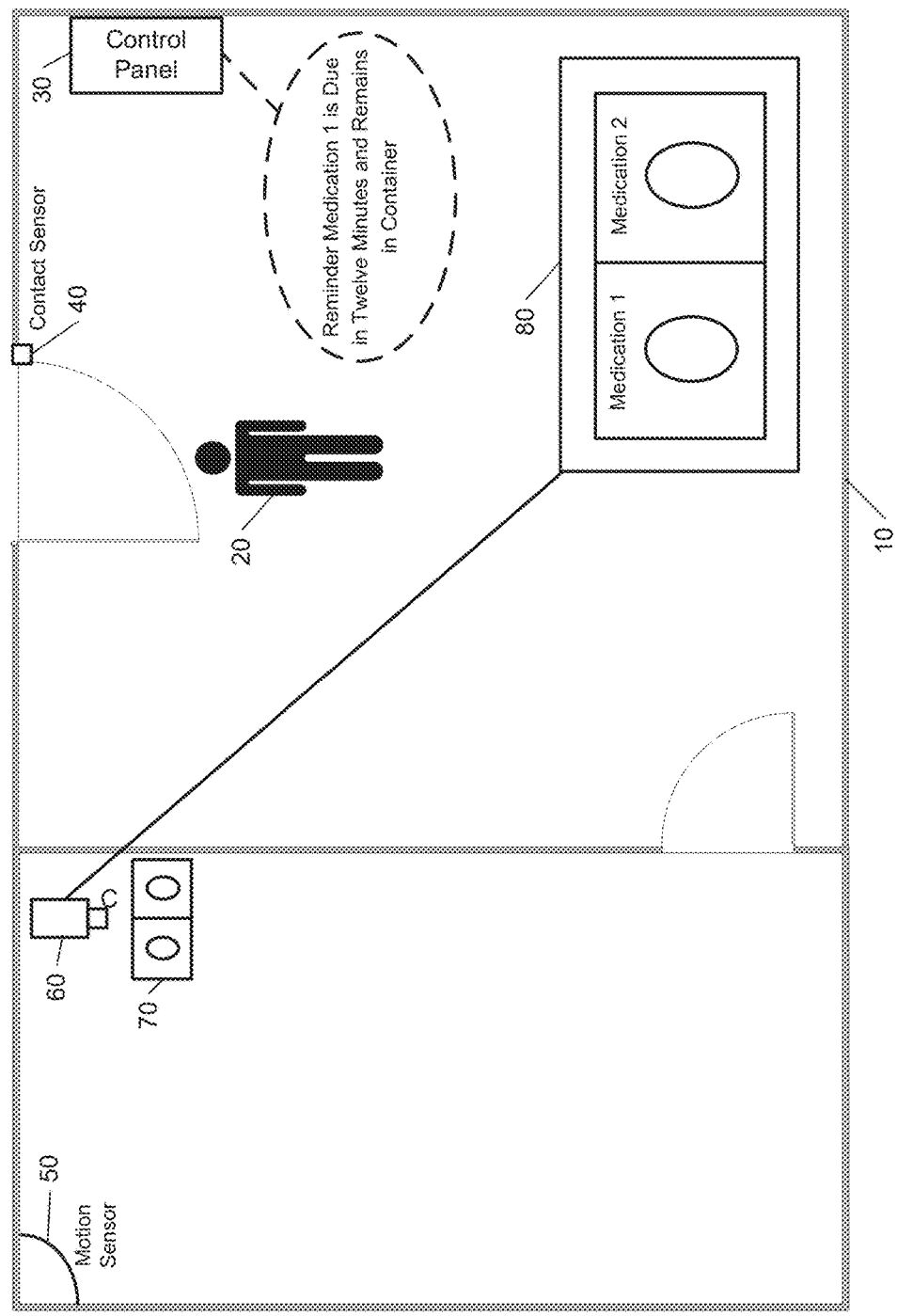

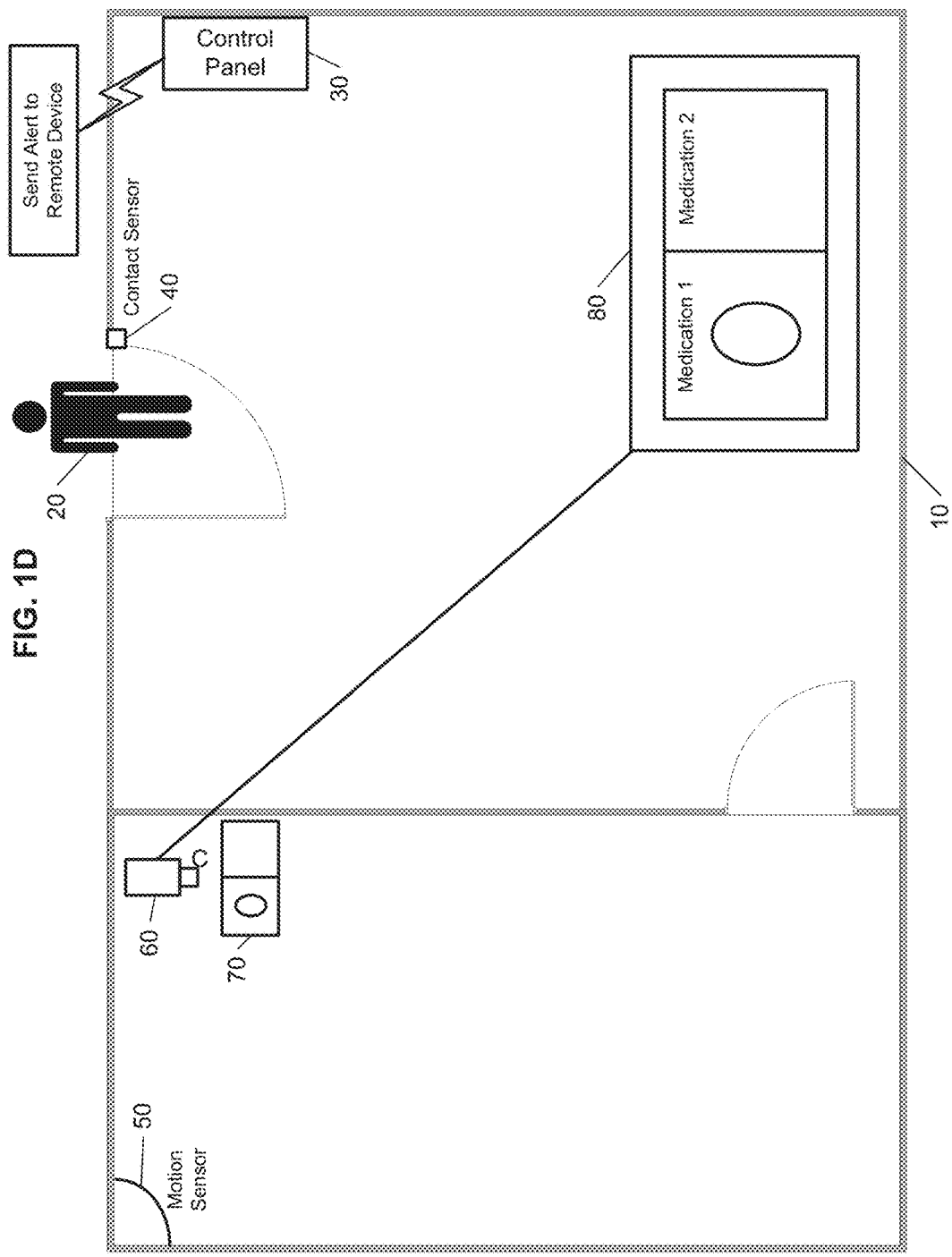

800

Reminder

You are scheduled to take Medication 1 and Medication 2 at 2:00 PM (15 minutes from now)

Will you take medication at scheduled time?

Yes — 810

If not, please enter time by which you will take medication.

820 — [        ]    Submit — 830

Note – Failure to respond will result in an alert being sent to your caregiver.

Alert

Sleep habits indicate that patient is not taking anti-depressant medication.

| Contact Patient | View Records | Increase Monitoring |
|---|---|---|
| 1211 | 1212 | 1213 |

1220

Alert

Bathroom habits indicate that medication patient is taking for urinary tract infection is not working.

| Prescribe New | Change Dosage | View Records | Contact Patient |
|---|---|---|---|
| 1221 | 1222 | 1223 | 1224 |

1230

Alert

Increase in pain reliever consumption indicates that headaches are a side effect of new medication for patient.

| Prescribe New | Change Dosage | View Records | Contact Patient |
|---|---|---|---|
| 1231 | 1232 | 1233 | 1234 |

FIG. 12

| Activity in Home | Degree | Past Consumption History | Alert Type |
|---|---|---|---|
| Yes | Low | Poor | In Home Alert |
| No | Moderate | Strict | Alert Remote Caregiver |
| Yes | Potentially Lethal | Average | Alert Emergency Services; Alert Remote Caregiver; In Home Alert |

MEDICATION MANAGEMENT AND REPORTING TECHNOLOGY

CROSS REFERENCE TO RELATED APPLICATIONS

This application is a continuation (and claims the benefit of priority under 35 USC § 120) of U.S. patent application Ser. No. 14/754,136, filed Jun. 29, 2015, now allowed, which is a continuation of U.S. application Ser. No. 14/461, 702, filed Aug. 18, 2014, now U.S. Pat. No. 9,070,267 issued Jun. 30, 2015, which is a continuation of U.S. application Ser. No. 13/439,703, filed Apr. 4, 2012, now U.S. Pat. No. 8,810,408, issued Aug. 19, 2014, which claims the benefit of U.S. Provisional Application No. 61/471,355, filed Apr. 4, 2011. All of these prior applications are incorporated herein by reference in their entirety for all purposes.

TECHNICAL FIELD

This disclosure relates to medication management and reporting technology.

BACKGROUND

Medication compliance, the adherence to clinically prescribed instructions of medication dosage and timing, is important for health and wellness. A host of factors can affect medication compliance, including but not limited to: confusion, forgetfulness, physical limitations, real or perceived side-effects, and medication availability (e.g., due to lack of refills). A decrease in compliance can have serious consequences for an individual, such as onset or exacerbation of illness and possible death. In the senescent population, for whom physical and mental disability are the most prevalent, resultant poor medication compliance can hasten the need for managed care—an undesirable outcome for independent living. Therefore, effective medication management and reporting is useful for both those receiving care and those giving care.

Care recipients and caregivers are often separated by distance or by time (e.g., because of incompatible schedules). Despite the best intentions of the most diligent caregivers, it is often difficult to remind and manage medication routines in person, at all times throughout the day. Moreover, such diligent oversight can be perceived as burdensome or obtrusive to those receiving care. Thus, many caregivers lack complete awareness about the medication routines of those they care for, and consequently, are unable to provide necessary assistance when compliance issues arise.

SUMMARY

Techniques are described for medication management and reporting technology. In one aspect, a method includes monitoring output from at least one sensor configured to sense physical activity in a building in which medication of a patient is located and, based on the monitoring of output from the at least one sensor, determining to collect additional information regarding the medication. The additional information is different than output from the at least one sensor. The method also includes collecting the additional information regarding the medication based on the determination to collect the additional information regarding the medication and analyzing the additional information collected to detect a state of the medication at a time of collecting the additional information. The method further includes accessing information regarding a schedule by which the medication should be taken by the patient and, based on the accessed information regarding the schedule, determining an expected state of the medication at the time of collecting the additional information that complies with the schedule by which the medication should be taken by the patient. In addition, the method includes comparing the detected state of the medication with the expected state of the medication that complies with the schedule and, based on the comparison revealing that the detected state of the medication does not match the expected state of the medication, determining that the patient has departed from the schedule. Based on the determination that the patient has departed from the schedule, a processing device handles the departure from the schedule.

Implementations may include one or more of the following features. For example, the method may include monitoring output of a motion sensor configured to detect motion in a room in which the medication is located, detecting motion in the room in which the medication is located based on the output of the motion sensor, and determining to collect additional information regarding the medication based on the detection of motion in the room in which the medication is located. The method also may include determining, based on the comparison of the detected state of the medication with the expected state of the medication, a degree of the departure from the schedule, determining a destination for a message indicating the departure from the schedule based on the determined degree of departure, and sending the message indicating the departure from the schedule to the determined destination.

In some implementations, the method may include determining to capture one or more images of the medication and capturing, with a camera positioned to include the medication within a field of view of the camera, an image of the medication. In these implementations, the method may include analyzing the captured image of the medication to detect a state of the medication at a time of capturing the image and determining an expected state of the medication at the time of capturing the image that complies with the schedule by which the medication should be taken by the patient.

The medication may be contained in a divided tray and the method may include analyzing the captured image of the medication to detect positions of the medication within the divided tray. The method also may include determining, based on the accessed information regarding the schedule, proper positions for the medication within the divided tray at the time of capturing the image that comply with the schedule by which the medication should be taken by the patient and comparing the detected positions of the medication within the divided tray with the proper positions for the medication within the divided tray. The method further may include determining that the detected positions of the medication within the divided tray do not match the proper positions for the medication within the divided tray based on the comparison of the detected positions of the medication within the divided tray with the proper positions for the medication within the divided tray and determining that the patient has departed from the schedule based on the determination that the detected positions of the medication within the divided tray do not match the proper positions for the medication within the divided tray.

In some examples, the medication is contained in one or more standard medication bottles and the method may include analyzing the captured image of the medication to identify the one or more standard medication bottles and detect positions within the captured image of the one or more standard medication bottles. In these examples, the method may include determining, based on the accessed information regarding the schedule, a proper medication bottle of the one or more standard medication bottles with which the patient should interact at the time the image is captured and comparing the detected positions within the captured image of the one or more standard medication bottles with the proper medication bottle with which the patient should interact at the time the image is captured. Further, in these examples, the method may include determining that the detected positions within the captured image of the one or more standard medication bottles suggest that the patient failed to interact with the proper medication bottle based on the comparison of the detected positions within the captured image of the one or more standard medication bottles with the proper medication bottle with which the patient should interact at the time the image is captured and determining that the patient has departed from the schedule based on the determination that the detected positions within the captured image of the one or more standard medication bottles suggest that the patient failed to interact with the proper medication bottle.

In some implementations, the method may include determining to request the patient to provide additional information regarding consumption of the medication using a user interface device of the patient, requesting the additional information from the patient, and determining the additional information regarding consumption of the medication based on any response received from the user interface device of the patient. In these implementations, the method may include analyzing the determined additional information regarding consumption of the medication to detect a state of the medication at a time of requesting the additional information from the patient and determining an expected state of the medication at the time of requesting the additional information from the patient that complies with the schedule by which the medication should be taken by the patient.

In some examples, the method may include monitoring activity of the patient, comparing the monitored activity of the patient with a routine of taking medication associated with the patient, determining an expectation that the patient will take the medication at a next appropriate time that complies with the schedule based on the comparison of the monitored activity of the patient with the routine of taking medication associated with the patient, and providing a reminder to take the medication at the next appropriate time that complies with the schedule based on determining that the patient is expected to miss taking the medication at the next appropriate time that complies with the schedule. In these examples, the method may include withholding the reminder to take the medication at the next appropriate time and continuing to monitor the activity of the patient based on determining that the patient is expected to take the medication at the next appropriate time that complies with the schedule.

Also, the method may include determining past medication consumption history related to the patient's taking of medication in accordance with the schedule by which the medication should be taken by the patient and comparing the monitored activity of the patient with the past medication consumption history and the schedule by which the medication should be taken by the patient. Further, the method may include monitoring a location of a mobile device used by the patient, monitoring output of at least one motion sensor of a monitoring system that monitors the building in which medication of the patient is located, and monitoring output of at least one contact sensor of the monitoring system that monitors the building in which medication of the patient is located.

In addition, the method may include providing a reminder to the patient that includes one or more user interface controls that enable the patient to indicate a time by which the patient expects to take the medication and receiving, based on user input provided by the patient using the one or more user interface controls, an indication of a time by which the patient expects to take the medication. The time by which the patient expects to take the medication may be after the next appropriate time that complies with the schedule. The method also may include determining that the time by which the patient expects to take the medication is within an acceptable range from the next appropriate time that complies with the schedule and, based on the determination that the time by which the patient expects to take the medication is within the acceptable range from the next appropriate time that complies with the schedule, adjusting the schedule based on the indication of the time by which the patient expects to take the medication. The method further may include handling verification of consumption of the medication and alerting related to consumption of the medication based on the adjusted schedule.

In some examples, the method may include monitoring, over time, activity of the patient during a period of time in which the patient is scheduled to take the medication, determining past activity of the patient, and analyzing the monitored activity of the patient during the period of time in which the patient is scheduled to take the medication with respect to the past activity of the patient. In these examples, the method may include determining whether an issue exists related to the patient's taking of the medication based on the analysis of the monitored activity of the patient during the period of time in which the patient is scheduled to take the medication with respect to the past activity of the patient and providing an alert based on a determination that an issue exists related to the patient's taking of the medication.

In some implementations, the method may include monitoring, over time, activity of the patient during a period of time in which the patient is scheduled to take the medication, determining expected activity of the patient during the period of time in which the patient is scheduled to take the medication, and analyzing the monitored activity of the patient during the period of time in which the patient is scheduled to take the medication with respect to the expected activity of the patient during the period of time in which the patient is scheduled to take the medication. In these implementations, the method may include determining whether an issue exists related to the patient's taking of the medication based on the analysis of the monitored activity of the patient during the period of time in which the patient is scheduled to take the medication with respect to the expected activity of the patient during the period of time in which the patient is scheduled to take the medication and providing an alert based on a determination that an issue exists related to the patient's taking of the medication.

The method may include monitoring, over time, activity of the patient during a period of time in which the patient is scheduled to take the medication, determining past activity of the patient, determining expected activity of the patient during the period of time in which the patient is scheduled to take the medication, and analyzing the monitored activity of the patient during the period of time in which the patient is scheduled to take the medication with respect to the past activity of the patient and the expected activity of the patient during the period of time in which the patient is scheduled to take the medication. The method also may include determining whether an issue exists related to the patient's taking of the medication based on the analysis of the monitored activity of the patient during the period of time in which the patient is scheduled to take the medication with respect to the past activity of the patient and the expected activity of the patient during the period of time in which the patient is scheduled to take the medication and providing an alert based on a determination that an issue exists related to the patient's taking of the medication. The method further may include determining whether the analysis indicates that the patient is not taking the medication, determining whether the analysis indicates that the medication is not working as expected, and determining whether the analysis indicates that the medication is causing the patient to suffer one or more side effects. In addition, the method may include providing an alert that indicates that the patient is not taking the medication based on a determination that the analysis indicates that the patient is not taking the medication, providing an alert that indicates that the medication is not working as expected based on a determination that the analysis indicates that the medication is not working as expected, and providing an alert that indicates that the medication is causing the patient to suffer one or more side effects based on a determination that the analysis indicates that the medication is causing the patient to suffer one or more side effects.

In addition, the method may include determining past medication consumption history related to the patient's taking of medication in accordance with the schedule by which the medication should be taken by the patient and handling the departure from the schedule based on the past medication consumption history related to the patient's taking of medication in accordance with the schedule. The method also may include determining activity of the patient and at least one caregiver after determining the departure from the schedule and handling the departure from the schedule based on the activity of the patient and at least one caregiver after determining the departure from the schedule.

In some implementations, the method may include determining whether activity exists within the building in which the medication of the patient is located after determining the departure from the schedule. In these implementations, the method may include, based on a determination that activity does not exist within the building in which the medication of the patient is located, providing a remote alert to a remote device that is located outside of the building. Also, in these implementations, the method may include, based on a determination that activity exists within the building in which the medication of the patient is located, providing a local alert within the building and monitoring for a confirmation in response to the local alert. The confirmation may indicate that the departure from the schedule is being handled. Further, in these implementations, the method may include, based on monitoring for the confirmation, determining that the confirmation has not been received within a threshold amount of time after providing the local alert and escalating the local alert to the remote alert to the remote device that is located outside of the building based on the determination that the confirmation has not been received within the threshold amount of time after providing the local alert.

In some examples, the method may include determining, based on the comparison of the detected state of the medication with the expected state of the medication, a degree of the departure from the schedule and determining past medication consumption history related to the patient's taking of medication in accordance with the schedule by which the medication should be taken by the patient. In these examples, the method may include determining activity of the patient and at least one caregiver after determining the departure from the schedule and handling the departure from the schedule based on the determined degree of the departure from the schedule, the past medication consumption history related to the patient's taking of medication in accordance with the schedule, and the activity of the patient and at least one caregiver after determining the departure from the schedule.

Implementations of the described techniques may include hardware, a method or process implemented at least partially in hardware, or a computer-readable storage medium encoded with executable instructions that, when executed by a processor, perform operations.

The details of one or more implementations are set forth in the accompanying drawings and the description below. Other features will be apparent from the description and drawings, and from the claims.

DESCRIPTION OF DRAWINGS

FIGS. 1A to 1D are diagrams of an example implementation.

FIG. 8 illustrates an example reminder interface.

FIG. 12 illustrates example alert interfaces.

FIG. 14 illustrates an example data structure used in providing alerts.

DETAILED DESCRIPTION

Figure 1B:
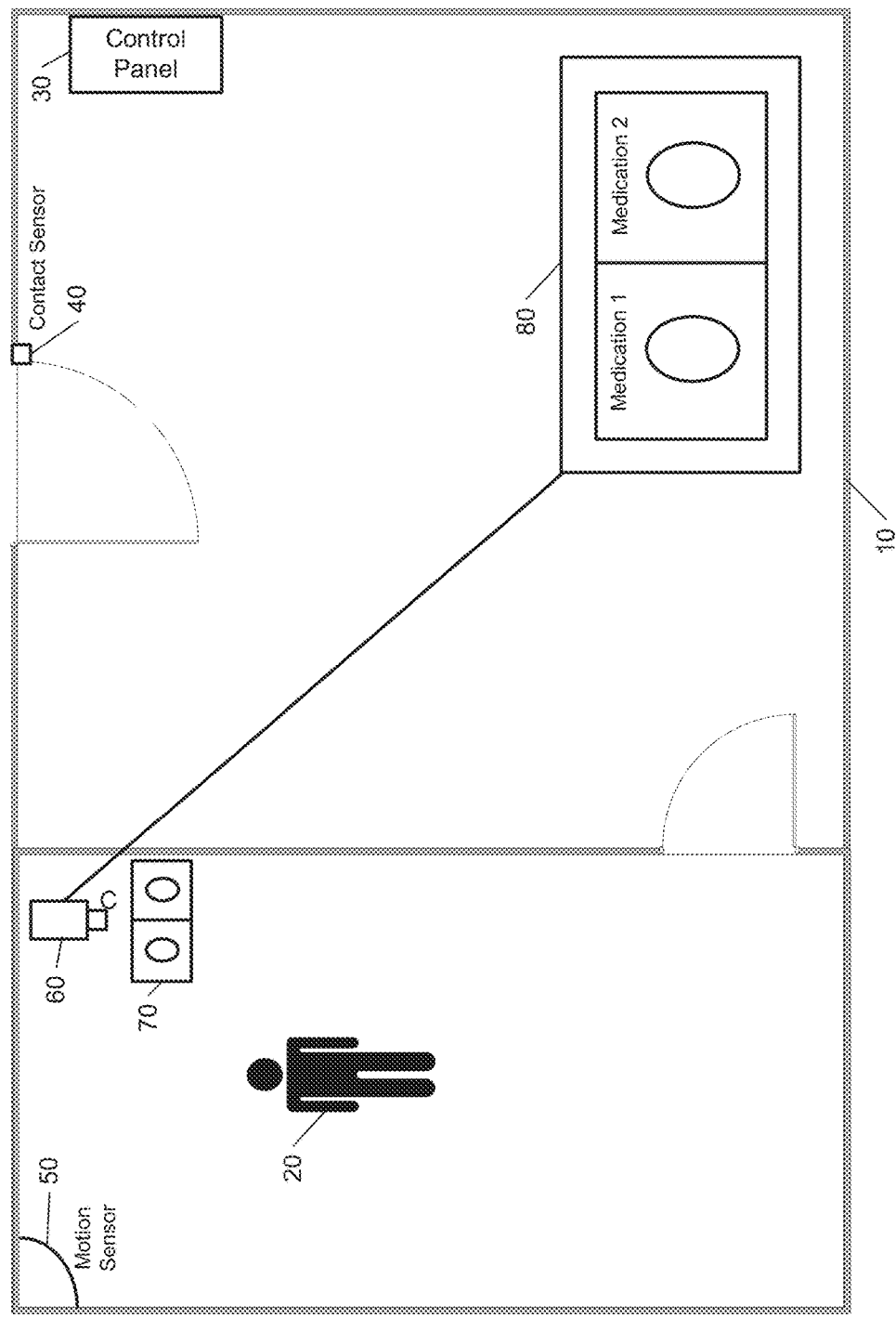

Techniques are described for addressing the aforementioned medication management and reporting challenges. FIGS. 1A to 1D illustrate an example implementation of medication management and reporting. As shown in FIG. 1A, a home 10 of a person 20 is monitored by a monitoring system (e.g., a home security system). The monitoring system includes a control panel 30 that controls operations of the monitoring system and provides an interface for a user to provide input to the monitoring system or receive output from the monitoring system. The control panel 30 is connected to a contact sensor 40 that detects whether an exterior door of the home 10 is oriented in an open position or a closed position. The connection between the control panel 30 and the contact sensor 40 may be a wired connection or a wireless connection. The control panel 30 receives output from the contact sensor 40 and determines whether the exterior door is oriented in an open position or a closed position based on the received output from the contact sensor 40.

The control panel 30 also is connected to a motion sensor 50 that detects motion in a room of the home 10 in which a camera 60 and a medication tray 70 are located. The motion sensor 50 detects motion proximate to the camera 60 and the medication tray 70 and provides output to the control panel 30 based on detected motion. The connection between the control panel 30 and the motion sensor 50 may be a wired connection or a wireless connection. The control panel 30 receives output from the motion sensor 50 and determines whether an object (e.g., a person) is moving in an area near the medication tray 70 based on the received output from the motion sensor 50.

The control panel 30 further is connected to the camera 60. The camera 60 is positioned to have the medication tray 70 within its field of view and the camera 60 captures images of the medication tray 70. The control panel 30 provides commands to control the camera 60 to capture images of the medication tray 70 and the control panel 30 receives output from the camera 60. The output received by the control panel 30 may be the images captured by the camera 60 and the control panel 30 may process the captured images to determine a state of the medication in the medication tray 70. Alternatively, the camera 60 may process the captured images to determine a state of the medication in the medication tray 70 and provide output to the control panel 30 that indicates the state of the medication in the medication tray 70. The connection between the control panel 30 and the camera 60 may be a wired connection or a wireless connection.

In the example shown in FIG. 1A, the person 20 has opened the exterior door to leave the home 10. The contact sensor 40 senses the exterior door changing to the open position and provides output to the control panel 30 indicating that the exterior door is oriented in the open position. The control panel 30 receives the output from the contact sensor 40 and determines that the exterior door has been opened. Because opening of the exterior door suggests that the person 20 is leaving the home 10, the control panel 30 initiates a process to check the state of the medication for the person 20 based on the determination that the exterior door has been opened. In this regard, the control panel 30 sends a command to the camera 60 to capture an image 80 of the medication in the medication tray 70 and also accesses, from a schedule that defines when the medication should be taken by the patient, information defining a proper state of the medication at a time of capturing the image and any medication events that are scheduled to occur in the relatively near future.

For instance, the control panel 30 determines that, at the time of capturing the image, the medication tray 70 should be filled with Medication One and Medication Two, determines that the next medication event for Medication One is in twelve minutes, and determines that the next medication event for Medication Two is in four hours. The control panel 30 analyzes the image 80 captured by the camera 60 and determines that the state of the medication tray 70 is filled with Medication One and Medication Two at the time of capturing the image. The control panel 30 compares the determined state of the medication to the proper state of the medication defined by the schedule and, based on the comparison, determines that the determined state of the medication matches the proper state. Thus, the control panel 30 determines that a missed medication event has not occurred and does not provide an alert for a missed medication event.

The control panel 30 also analyzes the scheduled medication events in relation to the sensor data that initiated the process to check the state of the medication for the person 20 (i.e., the output from the contact sensor 40). In this example, the control panel 30 compares the timing of the next scheduled medication events to a threshold that is set for determining whether or not to remind the person 20 of the next scheduled medication events. The threshold may be set based on user input, may be pre-set by a manufacturer or installer of the control panel 30, or may be set based on monitored activity of the person 20 over time. For instance, the control panel may analyze past output from the contact sensor 40 and determine that the person 20 leaves the home 10 for an average of one hour when the person 20 exits the home through the exterior door. Based on the determination that the person 20 leaves the home 10 for an average of one hour when the person 20 exits the home through the exterior door, the control panel 30 sets the threshold at one hour because it is relatively unlikely that the person 20 will complete a medication event that is scheduled for less than an hour after the person 20 exits the home through the exterior door and it is relatively likely that the person 20 will complete a medication event that is scheduled for more than an hour after the person 20 exits the home through the exterior door. Accordingly, the control panel 30 compares the time remaining until the next medication event for Medication One to the threshold of one hour and also compares the time remaining until the next medication event for Medication Two to the threshold of one hour. In this example, the control panel 30 determines that the time remaining until the next medication event for Medication One (i.e., twelve minutes) is less than the threshold and the control panel 30 determines that the time remaining until the next medication event for Medication Two (i.e., four hours) is more than the threshold.

Based on the determination that the time remaining until the next medication event for Medication Two (i.e., four hours) is more than the threshold, the control panel 30 determines to withhold a reminder for the next medication event for Medication Two. However, based on the determination that the time remaining until the next medication event for Medication One (i.e., twelve minutes) is less than the threshold, the control panel 30 provides a reminder for the next medication event for Medication One. As shown, the control panel 30 uses a speaker to provide an audible alert that reminds the person 20 that Medication One is due to be taken in twelve minutes and remains in the medication tray 70. Because the processing performed by the control panel 30 is relatively quick, the control panel 30 provides the alert prior to or just as the person 20 is exiting the home 10 through the exterior door. By providing an alert in this manner, the control panel 20 assists the person 20 in managing his or her medication because the person 20 is able to decide whether the person 20 should take Medication One with him or her as he or she leaves the home 10, take Medication One early since the next event is soon, or plan to return to the home 10 in twelve minutes to complete the next medication event.

As shown in FIG. 1B, the person 20 decides to take Medication One with him or her as he or she leaves the home 10 and enters the room in which the medication is located. Based on the person 20 entering the room in which the medication is located, the motion sensor 50 detects motion 50 near the medication tray 70 and sends output to the control panel 30 indicating that motion has been detected near the medication tray 70. In response to the output indicating that motion has been detected near the medication tray 70, the control panel 30 sends a command to the camera 60 to begin capturing images of the medication in the medication tray 70. To save battery power and cost, in some implementations, the camera 60 does not continuously capture images of the medication tray 70. Instead, the camera 60 waits for signals from the control panel 30 to capture images of the medication tray 70. The control panel 30 uses the output from sensors in the monitoring system (e.g., the contact sensor 40 and the motion sensor 50) and the schedule that defines when the person 20 should take medication to intelligently determine when images of the medication tray 70 should be taken. As shown in FIG. 1B, the person 20 has not reached the medication tray 70 and the control panel 30 analyzes the image 80 captured by the camera 60 and determines that the state of the medication tray 70 has not changed.

Figure 1C:
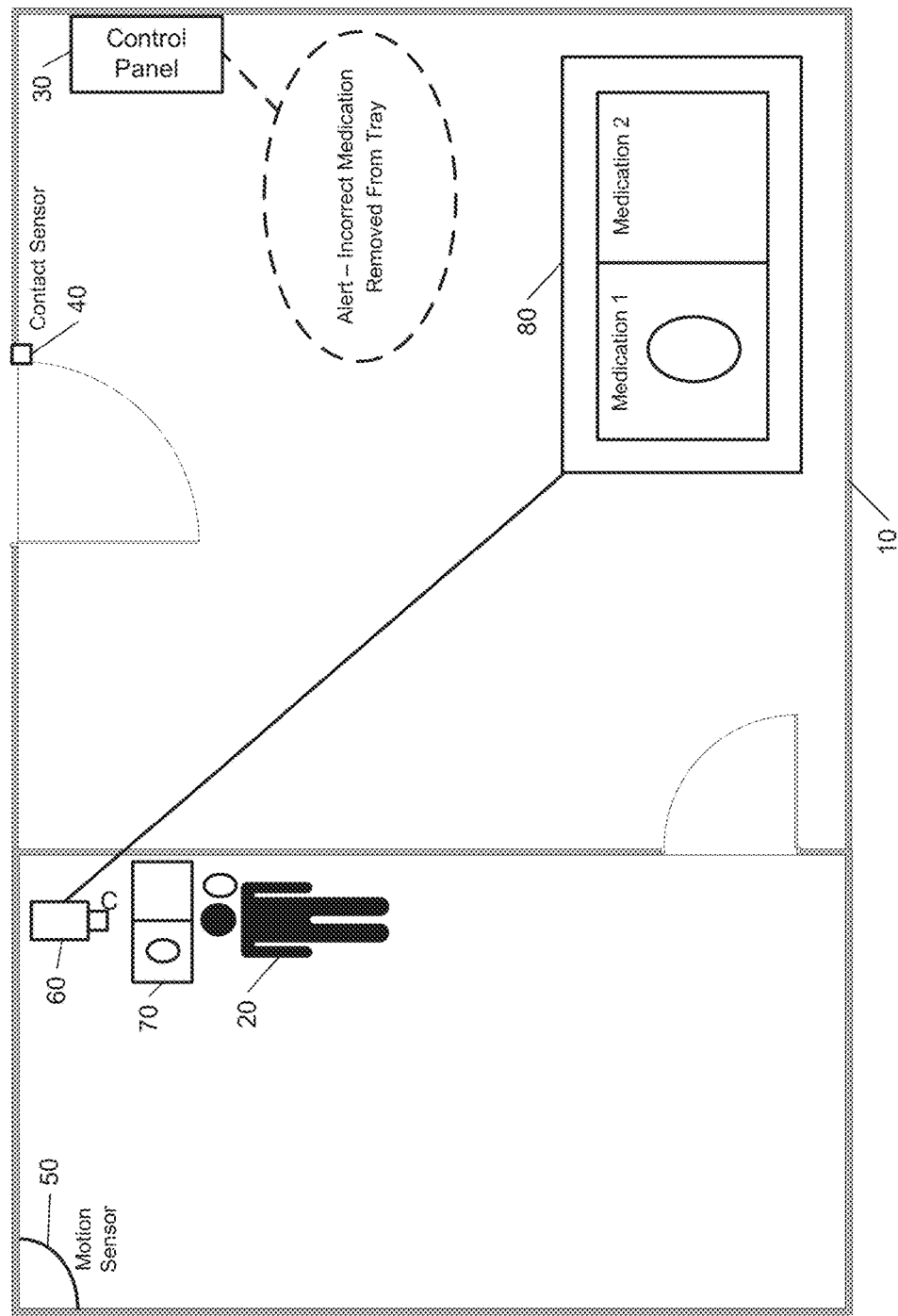

As shown in FIG. 1C, the person 20 arrives at the medication tray 70 and incorrectly takes Medication Two from the medication tray 70. During this time, the motion sensor 50 has continued to provide output indicating detected motion and the camera 60 has continued to capture images of the medication tray 70. The control panel 30 analyzes the image 80 captured by the camera 60 and determines that the state of the medication tray 70 has changed. Specifically, the control panel 30 determines that the state of the medication tray 70 is filled with Medication One and unfilled with Medication Two. The control panel 30 compares the determined state of the medication to the proper state of the medication (e.g., unfilled with Medication One and filled with Medication Two) defined by the schedule and, based on the comparison, determines that the determined state of the medication does not match the proper state. Thus, the control panel 30 determines that the person 20 has removed the incorrect medication from the medication tray 70 and provides an alert related to the removal of the incorrect medication. As shown, the control panel 30 uses a speaker to provide an audible alert that alerts the person 20 that the incorrect medication was removed from the medication tray 70. Because the next medication event for Medication One as defined by the schedule has not passed and the person 20 may have been removing the medication to consume at a later time after the person 20 has exited the home 10, the control panel 30 provides the audible alert in an attempt to alert the person 20 to the error and have the person 20 correct the error without having to involve a remote caregiver (or any other party). As the control panel 30 provides the audible alert, the control panel 30 continues to monitor the state of the medication and output from the contact sensor 40 to determine whether the person 20 corrects the error or exits the home 10 without correcting the error.

As shown in FIG. 1D, the person 20 has opened the exterior door and exited the home 10 without correcting the error. The control panel 30 detects that the person 20 opened the exterior door based on output from the contact sensor 40 and also confirms that the state of the medication in the medication tray 70 remains incorrect based on output from the camera 60. Based on the control panel 30 detecting that the person 20 opened the exterior door and confirming that the state of the medication in the medication tray 70 remains incorrect, the control panel 30 sends an alert to a remote device that is located outside of the home 10. The control panel 30 may send the alert to an intermediary monitoring server that processes the alert and, potentially, relays the alert to other devices. The control panel 30 also may send the alert to a central monitoring station that dispatches emergency services to assist with alarm situations or a remote device operated by a caregiver of the person 20 that is located outside of the home (e.g., at a nursing station or center). The control panel 30 further may send the alert to a mobile device operated by the person 20 or a mobile device operated by a family member of the person 20. The one or more alerts may indicate that the person 20 removed Medication Two at a time that does not accord with the person's medication schedule and that the person 20 has not removed Medication One in accordance with the person's medication schedule. The one or more alerts may assist the person 20 in correcting the medication error or assist the person 20 in getting help needed to address the medication error.

Figure 2:
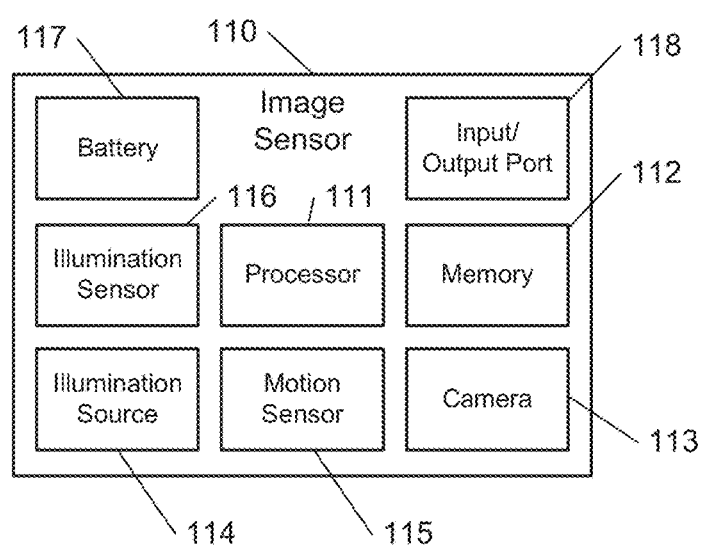
FIGS. 2 to 5 and 10 illustrate example systems.

FIG. 2 illustrates an image sensing device 110 that may be installed within a monitored home or facility. The image sensing device 110 combines multi-modal sensing (e.g., passive infrared motion sensor, triaxial inertial sensor, illumination sensor, etc.), an infrared illumination source, camera, processor, memory, battery, and input/output capabilities. The image sensing device 110 detects events indicative of mediation consumption (e.g., medication taken, medication missed, correct medication taken, incorrect medication taken, etc.).

The image sensing device 110 includes a processor 111, a memory 112, a camera 113, an illumination source 114, a motion sensor 115, an illumination sensor 116, a battery 117, and an input/output port 118. The processor 111 controls operations of the image sensing device 110 and may be any suitable processor. The memory 112 stores instructions that are executed by the processor 111 and also stores images captured by the camera 113. The memory 112 may be any type of memory that is capable storing data and may include a combination of multiple memory units. For example, the memory 112 may be a Flash memory component that stores both instructions that are executed by the processor and images captured by the camera 113.

The camera 113 captures images of an area proximate to where the image sensing device is located. For instance, the camera 113 may be placed at an upper corner of a room in a building and, in this instance, the camera 113 captures images of the room. The camera 113 also may be placed near medication pill bottles and capture images of movement near the bottles. The camera 113 may be a video/photographic camera or other type of optical sensing device configured to capture images. In some implementations, the camera 113 is a CMOS camera sensor (or a CCD sensor or any other type of imaging device) that captures images at various, different resolutions (e.g., low and/or high resolutions). For instance, the CMOS camera sensor may capture up to 640×480 pixels (e.g., VGA resolution). The camera 113 also may capture a lower resolution image (e.g., Quarter VGA=QVGA=320×240 pixels).

The illumination source 114 may be any source of illumination that improves capturing of images in a dark area. For example, the illumination source 114 may include one or more infrared LEDs that emit infrared light over an area within a field of view of the camera 113 to illuminate objects within the area. The processor 111 may control the illumination source 114 to emit light when the illumination sensor 116 detects a level of light that is below a threshold level.

The motion sensor 115 may be passive infrared (PIR) motion sensor, a microwave motion sensor, or any type of sensor that detects motion in an area corresponding to a field of view of the camera 113. The processor 111 may monitor output of the motion sensor 115 and trigger the camera 113 to capture images in response to the motion sensor 115 detecting motion in the area corresponding to the field of view of the camera 113.

The battery 117 is the power source of the image sensing device 110 and may be any type of battery capable of delivering power to the image sensing device 110. The battery 117 may have a relatively small size and may be a standard type of battery available for purchase at retail stores. The battery 117 may be located in a compartment that is easily accessible to a user of the image sensing device 110 to facilitate changing of the battery 117, which may occur relatively frequently (e.g., every couple of months) depending on the power consumption and image capture settings of the image sensing device 110.

The input/output port 118 is a communication interface through which the camera unit may send and receive wireless communications. The input/output port 118 may, using a short range wireless protocol (e.g., Bluetooth, Z-Wave, ZigBee, local wireless 900 MHz communication band, etc.), receive and send short range wireless communications with other devices. The input/output port 118 may include a "normally open" or "normally closed" digital input that can trigger capture of images using the camera 113.

To reduce processing power needed and to conserve battery life, the processor 111 may control components of the image sensing device 110 to periodically enter sleep mode operation. For example, the processor 111 may awaken every second to determine whether any communications have been received at the input/output port 118. If no communications have been received, the processor 111 may place itself and other components (e.g., the memory 112, the camera 113, etc.) in a sleep mode for another second before awaking again to determine whether any communications have been received at the input/output port 118. The processor 111 also may awaken from a sleep mode state based on output from the motion sensor 115 indicating that motion has been detected.

Figure 3:
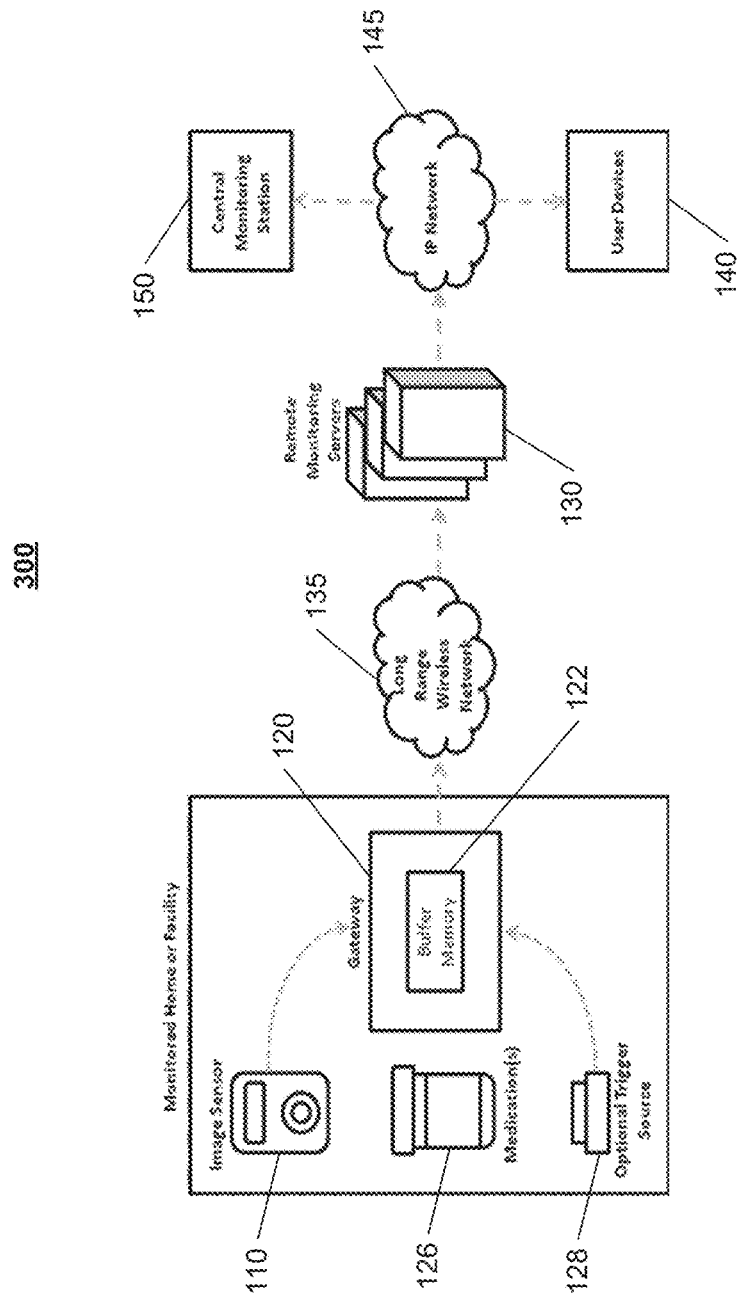

FIG. 3 illustrates an example of an electronic system 300 configured to provide medication management and reporting. The system 300 includes the image sensing device 110, a gateway 120, one or more remote monitoring servers 130, one or more user devices 140, and a central monitoring station 150. The image sensing device 110 is a relatively small and affordable unit that captures still images of an area that corresponds to a location of the camera unit. Because the image sensing device 110 is relatively small, runs off of battery power, and communicates via a wireless communication protocol, the image sensing device 110 may be easily placed at any location within a monitored property (or just outside of a monitored property) to provide image surveillance of an area of the monitored property (or an area just outside of the monitored property).

The gateway 120 is a communication device configured to exchange short range wireless communications with the image sensing device 110 and long range wireless or wired communications with the remote monitoring server 130 over the network 135. Because the gateway 120 exchanges short range wireless communications with the image sensing device 110, the gateway 120 is positioned nearby the image sensing device 110. As shown in FIG. 3, the gateway 120 and the image sensing device 110 are both located within a monitored property that is remote (and may be very far away from) the remote monitoring server 130.

In some examples, the gateway 120 may include a wireless communication device configured to exchange long range communications over a wireless data channel. In this example, the gateway 120 may transmit header data and image data over a wireless data channel. The gateway 120 may include one or more of a GSM module, a radio modem, cellular transmission module, or any type of module configured to exchange communications in one of the following formats: GSM or GPRS, CDMA, EDGE or EGPRS, EV-DO or EVDO, or UMTS.

The gateway 120 includes a buffer memory 122 that stores image data captured by the image sensing device 110. The buffer memory 122 may temporarily store image data captured by the image sensing device 110 to delay a decision of whether the image data (or a subset of the image data) is worthwhile to send to the remote monitoring server 130. The buffer memory 122 may be larger than the memory 112 of the image sensing device 110 and, because the gateway 120 operates using an AC power source, using the buffer memory 122 to store images captured by the image sensing device 110 may be more efficient. The gateway 120 also may include a display with which the stored images may be displayed to a user.

The long range wireless network 135 enables wireless communication between the gateway 120 and the remote monitoring server 130. The long range wireless network 135 may be any type of cellular network and may support any one or more of the following protocols: GSM or GPRS, CDMA, EDGE or EGPRS, EV-DO or EVDO, or UMTS. It may be relatively expensive to transmit data over the long range wireless network 135 and, therefore, the image sensing device 110 and the gateway 120 may be selective in the image data transmitted to the remote monitoring server 130.

The remote monitoring server 130 receives image data from the gateway 120 over the long range wireless network 135. The remote monitoring server 130 stores the received image data and makes the image data available to one or more user devices 140 and/or the central monitoring station 150 over the IP-based network 145. For instance, the remote monitoring server 130 may make the image data available to the one or more user devices 140 and/or the central monitoring station 150 at a website accessible by the one or more user devices 140 and/or the central monitoring station 150 over the Internet. The remote monitoring server 130 also may make the image data available to the one or more user devices 140 and/or the central monitoring station 150 in an electronic message, such as an electronic mail message.

In some implementations, the remote monitoring server 130 receives the image data from the gateway 120 as a reference image and a series of differential images that indicate the difference between the corresponding image and the reference image. In these implementations, header information sent with the image data indicates which images are reference images, which images are differential images, and which reference image each differential image corresponds to. The remote monitoring server 130 processes the reference image and the differential images and converts each image into a standard image format, such as JPEG. The remote monitoring server 130 then stores the converted images in a database or a file system and makes the converted images available to the one or more user devices 140 and/or the central monitoring station 150.

The central monitoring station 150 includes an electronic device (e.g., a server) configured to provide alarm monitoring service by exchanging communications with the remote monitoring server 130 over the network 145. For example, the central monitoring station 150 may be configured to monitor alarm events generated by a monitoring or alarm system that monitors the home or facility where the image sensing device 110 is located. In this example, the central monitoring station 150 may exchange communications with the remote monitoring server 130 to receive information regarding alarm events detected by the monitoring or alarm system. The central monitoring station 150 also may receive information regarding alarm events from the one or more user devices 140. The central monitoring station 150 may receive images captured by the image sensing device 110 to enable verification of potential alarm events associated with the proper use of medication.

The central monitoring station 150 may be connected to multiple terminals. The terminals may be used by operators to process alarm events. For example, the central monitoring station 150 may route alarm data to the terminals to enable an operator to process the alarm data. The terminals may include general-purpose computers (e.g., desktop personal computers, workstations, or laptop computers) that are configured to receive alarm data from a server in the central monitoring station 150 and render a display of information based on the alarm data. For example, the central monitoring station 150 may receive alarm data and route the alarm data to a terminal for processing by an operator associated with the terminal. The terminal may render a display to the operator that includes information associated with the alarm event (e.g., the name of the user of the alarm system, the address of the building the alarm system is monitoring, the type of alarm event, images of medication events taken of the image sensing device 110, etc.) and the operator may handle the alarm event based on the displayed information.

The one or more user devices 140 include devices that host user interfaces. For instance, the user devices 140 may include a mobile device that hosts one or more native applications (e.g., the medication monitoring and reporting application). The user devices 140 may include a cellular phone or a non-cellular locally networked device with a display. The user devices 140 may include a smart phone, a tablet PC, a personal digital assistant ("PDA"), or any other portable device configured to communicate over a network and convey information. For example, implementations may also include Blackberry-type devices (e.g., as provided by Research in Motion), electronic organizers, iPhone-type devices (e.g., as provided by Apple), iPod devices (e.g., as provided by Apple) or other portable music players, other communication devices, and handheld or portable electronic devices for gaming, communications, and/or data organization. The user devices 140 may perform functions unrelated to the monitoring system, such as placing personal telephone calls, playing music, playing video, displaying pictures, browsing the Internet, maintaining an electronic calendar, etc.

The user devices 140 may include a native medication monitoring and reporting application. The native medication monitoring and reporting application refers to a software/firmware program running on the corresponding mobile device that enables the user interface and features described throughout. The user devices 140 may load or install the native medication monitoring and reporting application based on data received over a network or data received from local media. The native medication monitoring and reporting application runs on mobile devices platforms, such as iPhone, iPod touch, Blackberry, Google Android, Windows Mobile, etc. The native medication monitoring and reporting application enables the user devices 140 to receive and process image and sensor data from the monitoring system.

The user devices 140 also may include a general-purpose computer (e.g., a desktop personal computer, a workstation, or a laptop computer) that is configured to communicate with the remote monitoring server 130 over the network 145. The user devices 140 may be configured to display a medication monitoring and reporting user interface that is generated by the user devices 140 or generated by the remote monitoring server 130. For example, the user devices 140 may be configured to display a user interface (e.g., a web page) provided by the remote monitoring server 130 that enables a user to perceive images captured by the image sensing device 110 and/or reports related to the monitoring system.

The system 300 further includes one or more medication containers 126 and one or more trigger sources 128. The medication containers 126 may be pill bottles or other containers or structures that are capable of storing medication for use by a patient. The medication containers 126 may be marked in an identifiable manner so that the system 300 can identify a particular medication container and distinguish between the different medication containers 126 used by a patient. For instance, the medication containers 126 may be different colors where a type of medication is associated with a color and the system 300 can determine which medicine is being taken by detecting the color of the medication container being used. The medication containers 126 also may have other identifying marks (e.g., bar codes) or the medication containers 126 may include other types of identification devices, such as radio-frequency identification (RFID) tags.

The trigger sources 128 may include devices or methods that detect medication events. For example, the trigger sources 128 may include contact or pressure sensors on which the medication containers 126 are placed when not in use. In this example, when a user picks up a medication container to take medication, one of the trigger sources 128 detects the medication event based on output from the contact or pressure sensor. The system 300 then triggers the image sensor 110 to capture images of the medication event for use in ensuring the proper medication is taken and the proper amount of medication is taken (e.g., not too little medication and not too much medication). The system 300 also may use output of the trigger sources 128 to identify which medication is being taken. In some implementations, the trigger sources 128 may include RFID detectors that detect RFID tags placed on the medication containers 126.

In some implementations, the image sensing device 110 and the gateway 120 may be part of a home or facility monitoring system (e.g., a home security system). In these implementations, the home or facility monitoring system may sense many types of events or activities associated with the home or facility and the sensed events or activities may be leveraged in performing medication monitoring and reporting features. The home or facility monitoring system may include a controller that communicates with the gateway 120. The controller may be configured to control the home or facility monitoring system (e.g., a home alarm or security system). In some examples, the controller may include a processor or other control circuitry configured to execute instructions of a program that controls operation of an alarm system. In these examples, the controller may be configured to receive input from sensors, detectors, or other devices included in the home or facility monitoring system and control operations of devices included in the home or facility monitoring system or other household devices (e.g., a thermostat, an appliance, lights, etc.).

The home or facility monitoring system also includes one or more sensors or detectors. For example, the home or facility monitoring system may include multiple sensors, including a contact sensor, a motion sensor or any other type of sensor included in an alarm system, security system, or monitoring system. The sensors also may include an environmental sensor, such as a temperature sensor, a water sensor, a rain sensor, a wind sensor, a light sensor, a smoke detector, a carbon monoxide detector, an air quality sensor, etc. The sensors further may include a health monitoring sensor, such as a prescription bottle sensor that monitors taking of prescriptions, a blood pressure sensor, a blood sugar sensor, a bed mat configured to sense presence of liquid (e.g., bodily fluids) on the bed mat, bathroom usage sensors, food consumption sensors, etc. In some examples, the sensors may include a radio-frequency identification (RFID) sensor that identifies a particular article that includes a pre-assigned RFID tag.

In addition, the system 300 may perform proactive care recipient guidance, reminders, and refills. To help encourage correct consumption and management of medications, several features are provided to assist those taking medications. For example, users can receive notifications preemptively reminding them to take medications prior to their scheduled times. Additionally, illumination, audio, or other user alerting devices within the installed home or facility can be employed to notify users to take a specific medication (e.g., reminder) or to alert them to one of various issues (e.g., medication bottle vacant, improper medication removal, medication bottle needing refill, etc.). All notification mechanisms (e.g., IVR, SMS, email, etc.) are possible user alerting devices. Also, information assessed from the analysis of medication reporting data can be used to remind users to refill medications or to signal third-parties (e.g., pharmacies, home care agents, caregivers, etc.) of the need for refills or to initiate refills. Contextual data can also be combined with other sensed data to make health or wellness assessments based on perceived compliance level and user activity.

In some examples, the system 300 may analyze data captured by other sensors (e.g., sensors of a home monitoring system) and determine how to report a medication event based on the analysis. In these examples, the system 300 may determine whether a property is occupied by one or more persons other than the medication recipient associated with a medication event and implement different reporting strategies depending on whether the property is occupied. For instance, the system 300 may provide a local alert or reminder (e.g., audible alert in the property) for a missed or improper medication event when the system 300 determines that the property is presently occupied. The system 300 may escalate the local alert to a remote alert or reminder (e.g., a message to a remote monitoring service that dispatches emergency services) if the system 300 determines that no corrective action has been taken for a threshold period of time (e.g., the system 300 does not detect a proper medication event or receive confirmation that the improper medication event is being handled for a threshold period of time). When the system 300 determines that the property is not presently occupied, the system 300 may send the remote alert or reminder in the first instance.

Historical data regarding medication compliance may be used in reporting analysis. The historical data may include information describing compliance with past medication schedules and past occupancy/usage data for the property. For example, the system 300 may determine that a first user adheres very strictly to a medication schedule based on compliance with past medication schedules and a second user does not adhere as strictly to a medication schedule, but typically complies with the medication schedule within permissible tolerances. In this example, the system 300 may send a heightened alert (e.g., a message to a remote monitoring service that dispatches emergency services) a short time after the system 300 detects that the first user misses a medication event, but may wait longer to send a heightened alert after the system 300 detects that the second user misses a medication event to allow the second user more time within the permissible tolerances. In another example, the system 300 may monitor past occupancy of the property and determine typical occupancy patterns for the property. In this example, the system 300 may use the typical occupancy patterns to infer whether the property is occupied at the time of a missed or improper medication and handle reporting for the missed or improper medication event based on the inference (e.g., as described above for examples in which occupancy of the property is detected directly).

In some implementations, the system 300 may assess how much medication was taken by a medication recipient and a type of the medication taken using techniques described throughout this disclosure. In one example, the system 300 may include a weight sensitive sensor that assesses how much medication has been removed (e.g., how many pills have been removed) during a medication event based on a weight difference between a container housing the medication before and after the medication event. In these implementations, the system 300 may take different actions based on how much medication was taken and/or what type of medication was taken. For instance, the system 300 may determine whether the amount of medication taken for the type of medication is a potentially lethal dosage or a non-lethal dosage (e.g., by referencing a dosage table prepared by a medical professional that describes what constitutes a potentially lethal versus non-lethal dosage of a medication for a person with characteristics of the medication recipient). If the system 300 determines that a potentially lethal dosage has been taken, the system 300 may immediately send a message to a remote monitoring service that dispatches emergency services. If the system 300 determines that a non-lethal, but incorrect, dosage has been taken, the system 300 may send a message indicating the incorrect medication event to a caregiver of the medication recipient, but withhold sending a message to a remote monitoring service that dispatches emergency services unless other events occur that warrant such a message. The system 300 may consider other medications the medication recipient is taking and past medication behavior of the medication recipient in determining whether a dosage is potentially lethal or non-lethal. For instance, the system 300 may determine that the medication recipient has taken a potentially lethal dosage of medication when the medication recipient takes a combination of medications at an amount that would be non-lethal if taken individually, but potentially lethal if taken together. Also, the system 300 may determine that the medication recipient has taken a potentially lethal dosage of medication when the medication recipient has taken multiple non-lethal, but incorrect, dosages of a medication, but has done so in a time period that results in a potentially lethal total dosage of medication.

In some examples, the system 300 may monitor all activities of daily living that are captured by sensors at a property (e.g., bathroom activity, sleep activity, eating habits, speed of movement, general level of activity, etc.) and analyze the monitored activities in an attempt to identify side effects of medication. In these examples, the system 300 may compare activity of a medication recipient before starting a new medication to activity of the medication recipient after starting the new medication. When the comparison reveals a difference in activity, the system 300 may report a potential side effect to the new medication.

Figure 4:
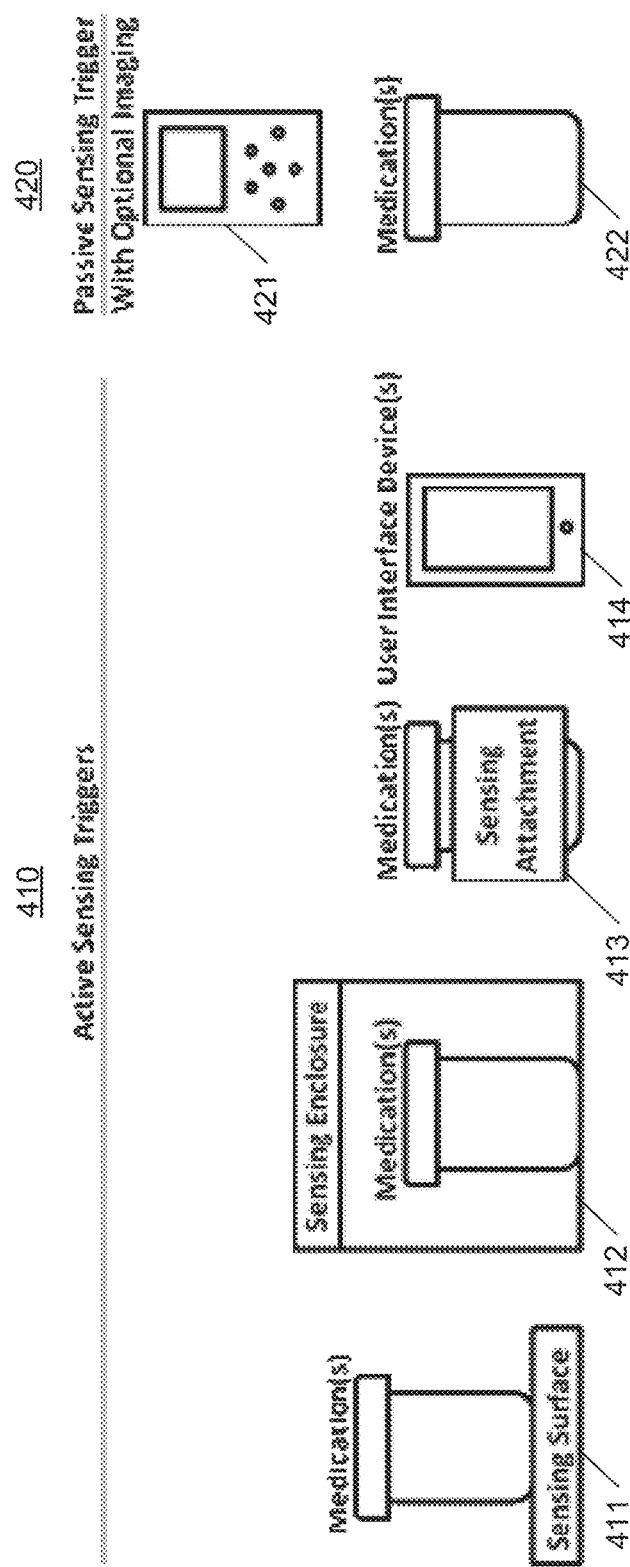

FIG. 4 illustrates example trigger sources. Any one or more of the example trigger sources shown in FIG. 4 may be used as the trigger source when the present description refers to use of a trigger source. A trigger source is a device capable of detecting the removal or use of a medication or medication container. Medications can remain in their original packaging or be placed inside of another container within a sensed region. The trigger technology may be active (e.g., requiring contact with the user, medication, or medication container) or passive (e.g., not in direct contact with the user, medication, or medication container). Physical incarnations of active trigger sources 410 may include, but are not limited to, a sensing surface 411 (activated by wireless communication, weight, reflected infrared, mechanical switch, magnetic, etc.), a sensing enclosure 412 (activated by mechanical switches, etc.), an attachment 413 to a sensing container (activated by wireless communication, movement, change in capacitance, mechanical switch, etc.), or user interface device 414 (activated by user input, near-field radio communication, wireless communication, etc.). The sensing surface 411 may be capable of recognizing the type of medication taken (by wireless communication such as near-field communication, radio-frequency identification, etc.) and the amount taken (by assessing change in weight of medication containers). Furthermore, physical incarnations of active sensing triggers 410 may be combined (e.g., pairing of sensing surface 411 and sensing attachment 413).

Passive trigger sources 420 (e.g., motion sensors, door sensors, and imaging devices) can detect possible user actions near, but not in direct contact with medication devices. For example, a motion sensor 421 with a restricted field of view can detect movement near a medication container 422. Also, a door sensor placed on a medication cabinet can detect possible medication removals.

Figure 5:
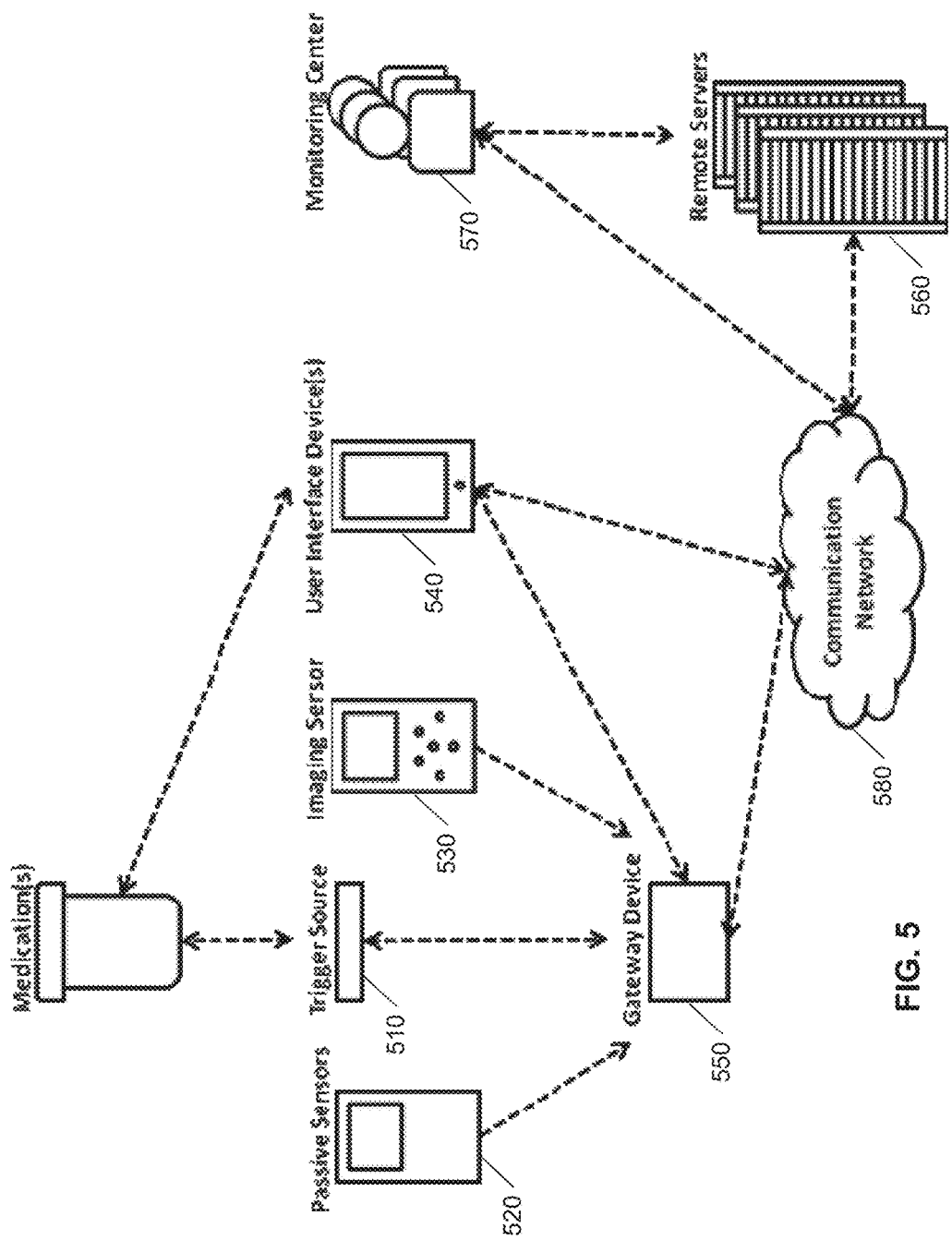

FIG. 5 illustrates another example of an electronic system 500 configured to provide medication management and reporting. The system 500 includes one or more trigger sources 510, one or more passive sensors 520, one or more imaging sensors 530, one or more user interface devices 540, a gateway device 550, one or more remote servers 560, and a monitoring center 570. The one or more user interface devices 540, the gateway device 550, the one or more remote servers 560, and the monitoring center 570 may exchange communications over a communication network 580.

In addition to their use as passive trigger sources, passive sensors 520 may be employed to monitor medication-related events or lack thereof. For example, passive sensors 520 can monitor aspects of behavior related to medication consumption (e.g., general activity level, sleeping, eating, bathroom use, etc.). This behavior profiling can help to promote behaviors necessary for certain medications (e.g., eating before or after consuming medications) or to assess the effects of certain medications (e.g., sleeping, bathroom use, etc.).

Imaging sensors 530 (e.g., still frame or video) are capable of recognizing the type of medication taken (by analyzing native or added markings affixed to the medication container). Furthermore, imaging sensors 530 paired with identify recognition routines can be utilized to identify an individual associated with a taken medication. Imaging sensors 530 may also have other modes of sensing (e.g., motion, acceleration, etc.) to trigger or augment native imaging and sensing capabilities.

A user interface device 540 can be used to communicate information to or gather information from a user about medications or medication-related activity (e.g., medications, schedules, reminders, verification, behavior profiling, or reporting). Possible physical incarnations of user interface devices 540 may include light or audio sources, displays, push buttons, or mobile devices (e.g., mobile phones or mobile phone applications). A user interface device 540 may also act as a sensing device and relay data to the gateway device 550 or directly to remote servers 560 through the communication network 580. For example, the user interface device 540 may actively seek a response from a patient (e.g., via push button) to confirm medication adherence or passively monitor activity with built-in sensors.

A gateway device 550 can be used to relay information between remote servers 560 (e.g., over a public or private communication network) and systems at the patient location. The gateway device 550 can also allow systems within a patient's location to communicate without involvement from remote servers 560. Certain incarnations of the system 500 may not include a gateway device 550. Therefore, trigger sources 510, passive sensors 520, imaging sensors 530, or user interface devices 540 may be connected directly to the communication network 580.

Remote servers 560 may be employed to store, process, and initiate actions based upon medication data collected about each monitored user and location. Monitoring center agents can also annotate user records stored on the remote servers 560.

A monitoring center 570 may employ automated or human agents to observe user medication events and contact users or caregivers based on defined protocols, quantitative or qualitative assessments. Monitoring center agents can also annotate records stored on the remote server 560 about a patient.

Figure 6:
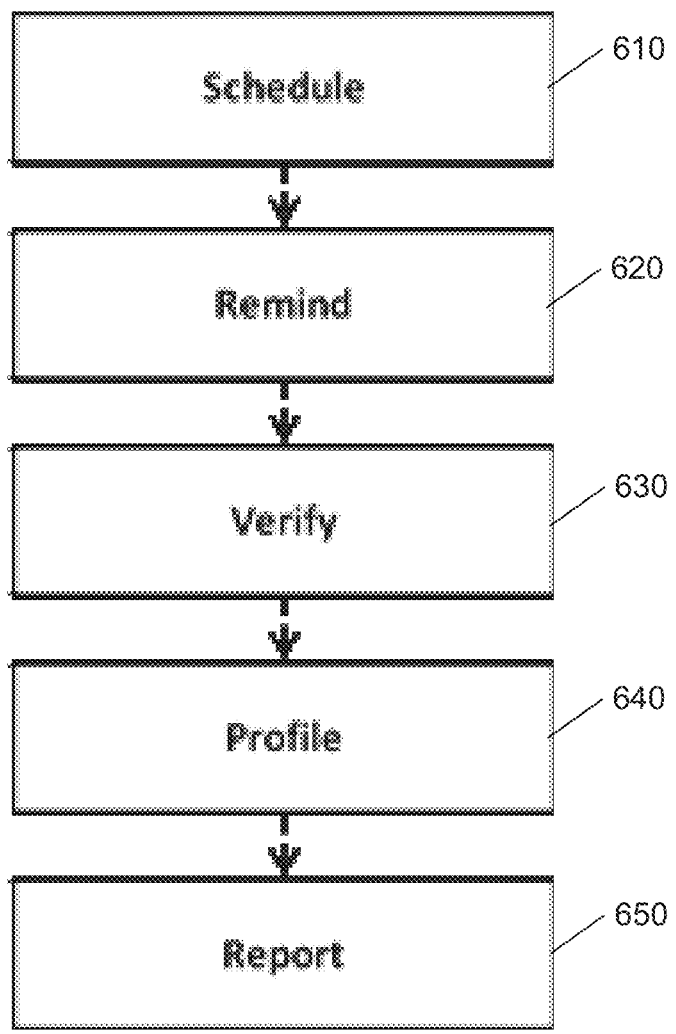
FIGS. 6, 7, 9, 11, and 13 are flow charts illustrating example processes.

FIG. 6 illustrates an example process 600 for medication monitoring and reporting. The operations of the example process 600 are described generally as being performed by the system 300. The operations of the example process 600 may be performed by one of the components of the system 300 (e.g., the image sensing device 110, the gateway 120, the remote monitoring server 130, etc.) or may be performed by any combination of the components of the system 300. The operations of the example process 600 also may be performed by the system 500 or one or more components of the system 500. In some implementations, operations of the example process 600 may be performed by one or more processors included in one or more electronic devices.

The process 600 for medication management includes scheduling (610), reminding (620), verifying (630), profiling (640), and reporting (650). Although multiple steps are illustrated as part of the overall process 600, some medication management implementations may only employ a subset of these steps.

The system 300 performs scheduling of one or more medication events (610). A medication event can be entered by a user (e.g., patient, formal caregiver, informal caregiver) into a user interface device or a website. The schedule can be stored on local devices and on remote servers. The schedule can also be downloaded from other prescription medication entities (e.g., pharmacies, prescription clearinghouse, electronic medical record, etc.). The user interface device can capture the schedule from visual inspection of the label (e.g., image processing from captured image) or wirelessly (e.g., radio-frequency identification or near-field communication tag on medication container). The user interface device can also derive information from other sensors (e.g., imaging sensor) or trigger sources to ascertain the schedule. The user interface device can synchronize schedules with the patient stored records on the remote server via a gateway device connected to a communication network or straight to the communication network. Schedules on the remote servers can be accessed by a monitoring center or other trusted entities.

The system 300 performs reminding related to one or more medication events (620). From predefined schedules, patients can be prompted preemptively to remind them to take medications prior to their scheduled times. This prompting can be initiated at the remote servers or at the user interface device. The prompting can employ user interface output mechanisms (e.g., audio, illumination, display, etc.) or communicate directly to the user via automated telephone call, text message, push notification, or email. Reminders can also be generated when medication refills are needed based on information stored at the server or on a user interface device. Reminders can be paired with patient queries (e.g., questionnaire in mobile application) to determine medication usage in the absence of sensors or trigger sources. Reminders can be sent to patients or caregivers.

Figure 7:
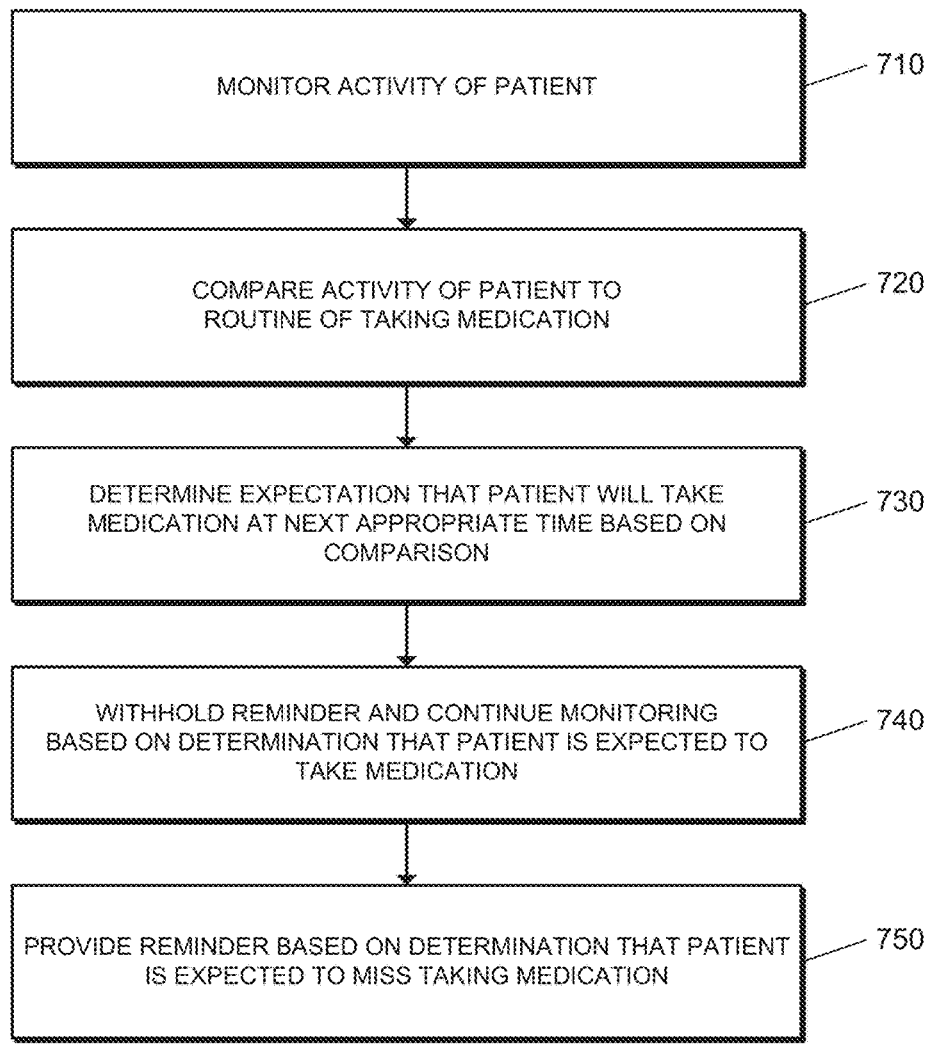

FIG. 7 illustrates an example process 700 for performing reminding related to one or more medication events. The operations of the example process 700 are described generally as being performed by the system 300. The operations of the example process 700 may be performed by one of the components of the system 300 (e.g., the image sensing device 110, the gateway 120, the remote monitoring server 130, etc.) or may be performed by any combination of the components of the system 300. The operations of the example process 700 also may be performed by the system 500 or one or more components of the system 500. In some implementations, operations of the example process 700 may be performed by one or more processors included in one or more electronic devices.

The system 300 monitors activity of a patient (710). For example, the system 300 monitors activity of the patient within the patient's home. In this example, the system 300 may monitor any of the sensors described throughout this disclosure to monitor the patient's activity within the patient's home. The system 300 may consider any data collected by a monitoring system that monitors the patient's home with the data considered being any of the sensor data (e.g., contact sensor data, motion sensor data, image sensor data, etc.) described throughout this disclosure.

In addition, the system 300 monitors activity of the patient outside of the patient's home. For instance, the system 300 may receive reports from a mobile device (e.g., mobile phone) of the patient that indicate a location of the mobile device determined using Global Positioning System (GPS) technology. The system 300 also may monitor activity of the patient outside of the patient's home using any other type of tracking device that is capable of tracking the patient's location outside of the patient's home.

The system 300 compares the monitored activity of the patient to a routine of taking medication associated with the patient (720). For example, the system 300 compares the monitored activity of the patient to a schedule of medication events for the patient. In this example, the system 300 evaluates the activity of the patient with respect to the next scheduled medication event for the patient to assess whether or not the activity of the patient suggests that the patient will be able to complete the next scheduled medication event.

The system 300 also may compare the monitored activity of the patient to past routine activity of the patient in completing scheduled medication events. For example, the system 300 may track the patient's activity over time in relation to the patient completing scheduled medication events. In this example, the system 300 may compare the monitored activity of the patient to a tracked routine of past activity of the patient when the patient has successfully completed medication events in the past. Based on the comparison of the monitored activity to the tracked routine of past activity for successful medication events, the system 300 determines whether the current monitored activity is consistent with the tracked routine of past activity for successful medication events or inconsistent with the tracked routine of past activity for successful medication events.

Further, the system 300 may compare the monitored activity of the patient to a tracked routine of past activity of the patient when the patient has not successfully completed medication events in the past. Based on the comparison of the monitored activity to the tracked routine of past activity for unsuccessful medication events, the system 300 determines whether the current monitored activity is consistent with the tracked routine of past activity for unsuccessful medication events or inconsistent with the tracked routine of past activity for unsuccessful medication events.

The system 300 determines an expectation that the patient will take medication at a next appropriate time based on the comparison (730). For instance, the system 300 evaluates the comparison of the monitored activity of the patient to the schedule of medication events for the patient and, based on the evaluation, determines whether or not the patient appears to be in position to successfully complete the next scheduled medication event. When the evaluation reveals that the next scheduled medication event is in fifteen minutes, the medication is within the patient's home, and the patient is detected as moving around the patient's home, the system 300 determines that the patient is likely to successfully complete the next scheduled medication event. When the evaluation reveals that the next scheduled medication event is in fifteen minutes, the medication is within the patient's home, and the patient is detected as being outside of the patient's home more than twenty miles away, the system 300 determines that the patient is likely to miss the next scheduled medication event. The system 300 also may consider whether the patient is leaving the patient's home at a time that is relatively close to the next scheduled medication event and determine that the patient is likely to miss the next scheduled medication event based on the patient leaving the patient's home at a time that is relatively close to the next scheduled medication event when the medication remains in the patient's home.

In addition, the system 300 may evaluate the comparison of the monitored activity of the patient to past routine activity of the patient in completing scheduled medication events and, based on the evaluation, determine whether or not the patient is likely to successfully complete the next scheduled medication event. For instance, the system 300 determines that the patient is likely to successfully complete the next scheduled medication event based on the evaluation revealing that the current monitored activity is consistent with the tracked routine of past activity for successful medication events. In contrast, the system 300 determines that the patient is likely to miss the next scheduled medication event based on the evaluation revealing that the current monitored activity is inconsistent with the tracked routine of past activity for successful medication events. Moreover, the system 300 determines that the patient is likely to miss the next scheduled medication event based on the evaluation revealing that the current monitored activity is consistent with the tracked routine of past activity for unsuccessful medication events.

The system 300 withholds a reminder and continues monitoring activity of the patient based on a determination that the patient is expected to take medication at the next appropriate time (740). For instance, the system 300 determines not to provide a reminder to the patient or the patient's caregiver based on a determination that the patient is likely to successfully complete the next scheduled medication event. By withholding the reminder, the system 300 does not burden the patient or the patient's caregiver with reminders when the patient is expected to successfully complete the next scheduled medication event. In this regard, the patient and the patient's caregiver are less likely to become annoyed with the system 300 and are more likely to take medication reminders provided by the system 300 seriously. The system 300 does continue monitoring the activity of the patient to determine whether the patient's activity changes and it becomes likely that the patient will miss the next scheduled medication event. If the system 300 determines that it becomes likely that the patient will miss the next scheduled medication event, the system 300 provides a reminder or alert as appropriate.

The system 300 provides a reminder based on a determination that the patient is expected to miss taking medication at the next appropriate time (750). For example, the system 300 provides a reminder to the patient or the patient's caregiver. In this example, the system 300 may determine whether the monitored activity suggests that the patient or the patient's caregiver is within the patient's home with the medication in determining how to provide the reminder. When the system 300 determines that the monitored activity suggests that the patient or the patient's caregiver is within the patient's home, the system 300 may first attempt an in home reminder using a speaker, display, or other output device that is part of the monitoring system in the patient's home. In this regard, the system 300 delays elevating the reminder to a remote caregiver or monitoring station because the patient or the patient's caregiver is located in the home and is likely to be in position to complete the medication event when reminded. When the system 300 determines that the monitored activity suggests that the patient is outside of the patient's home, the system 300 provides a reminder to a remote device (e.g., mobile phone) of the patient and also may provide a reminder to a remote caregiver or monitoring station to alert the remote caregiver or monitoring station that the patient is unlikely going to be able to complete the next scheduled medication event.

FIG. 8 illustrates an example reminder interface 800. The reminder interface 800 may be displayed by a device (e.g., a mobile device, a personal computer, etc.) operated by the patient. The reminder interface 800 provides an indication that the patient is scheduled to take two types of medication at 2:00 PM, which the reminder interface 800 indicates is fifteen minutes from when the reminder was provided. The reminder interface 800 also asks the patient to confirm that the medication will be taken at the scheduled time and provides an input control 810 to which the patient may provide user input to confirm that the medication will be taken at the scheduled time. Based on the patient providing user input confirming that the medication will be taken at the scheduled time, the system 300 may withhold further reminders until the scheduled time passes without the system 300 detecting completion of the medication event. In addition, the system 300 may delay alerting a remote caregiver or a monitoring station in the event of a missed medication event being detected based on the patient providing user input confirming that the medication will be taken at the scheduled time. For example, in response to detecting a missed medication event, the system 300 may first provide another reminder to the patient because the patient appears to be engaged in completing the medication event. In this example, the system 300 may continue to monitor for completion of the medication event after providing the additional reminder to the patient and then alert a remote caregiver or a monitoring station based on detecting that the medication event has not been completed within a threshold period of time after providing the additional reminder.

The reminder interface 800 also enables the patient to enter a time by which the patient will take medication when the patient is unable to take the medication by the scheduled time. For example, the reminder interface 800 includes an input area 820 in which the patient may enter the time by which the patient expects to be able to take the medication and an input control 830 that enables the patient to provide user input submitting the time entered in the input area 820. In this example, the patient may use the input area 820 and the input control 830 to enter a time by which the patient expects to take the medication that is after the scheduled time (e.g., the next appropriate time that complies with the schedule). Based on the patient entering a time that is after the scheduled time, the system 300 determines whether the entered time is within an acceptable range of the scheduled time (e.g., a range of time in which the taking of the medication will be substantially as effective as if taken at the scheduled time).

Based on a determination that the entered time is outside of the acceptable range of the scheduled time, the system 300 provides an alert to the patient indicating that the entered time is not acceptable and that the patient needs to take the medication by a time that is within the acceptable range. The system 300 also may provide an alert to a remote caregiver or a monitoring station alerting that the patient provided user input indicating that the patient is unable to take the medication within the acceptable range.

Based on a determination that the entered time is within the acceptable range of the scheduled time, the system 300 adjusts the schedule based on the entered time by which the patient expects to take the medication and handles verification of consumption of the medication and alerting related to consumption of the medication based on the adjusted schedule. For example, the system 300 resets the next scheduled time to the entered time by which the patient expects to take the medication and monitors whether the patient takes the medication by the reset time. In this example, the system 300 discontinues monitoring of the originally scheduled time and does not provide alerts or reminders when the originally scheduled time passes. Rather, the system 300 only provide alerts or reminders based on the system 300 detecting the reset time passing without detecting completion of the medication event.

The reminder interface 800 further includes an indication that a failure to respond will result in an alert being sent to a caregiver. The system 300 monitors for a response to the reminder and sends an alert to a remote caregiver or a monitoring station based on detecting that the patient has failed to respond to the reminder within a threshold period of time.

Referring again to FIG. 6, the system 300 performs verification related to one or more medication events (630). Verification of medication schedule can check whether the correct medication is taken at the correct time in the correct dosage by the intended patient. A medication event can be signaled by one or more trigger sources or user interface devices. An event can be detected proximal to the medication(s) by any of the aforementioned trigger sources and sensors, or a patient can communicate their compliance via user interface devices (e.g., push of a button, etc.). The event or events within a window of time can be compared to a stored schedule at the remote servers or locally on a user interface device. If medication is taken at the incorrect time or no medication event is triggered, the event or non-event can be flagged by the user interface device or at the remote servers. Subsequent immediate feedback (e.g., to the user interface device, automated or monitored telephone call, email, text message, etc.) can be initiated to the patient or caregivers.

Imaging devices, user interface devices, sensors, or trigger sources may also be used to verify the identity of the patient taking the medication passively (e.g. facial recognition at the device or remote server, etc.) or actively (e.g. biometric authentication, radio frequency identification or near field communication tags, etc.).

Figure 9:
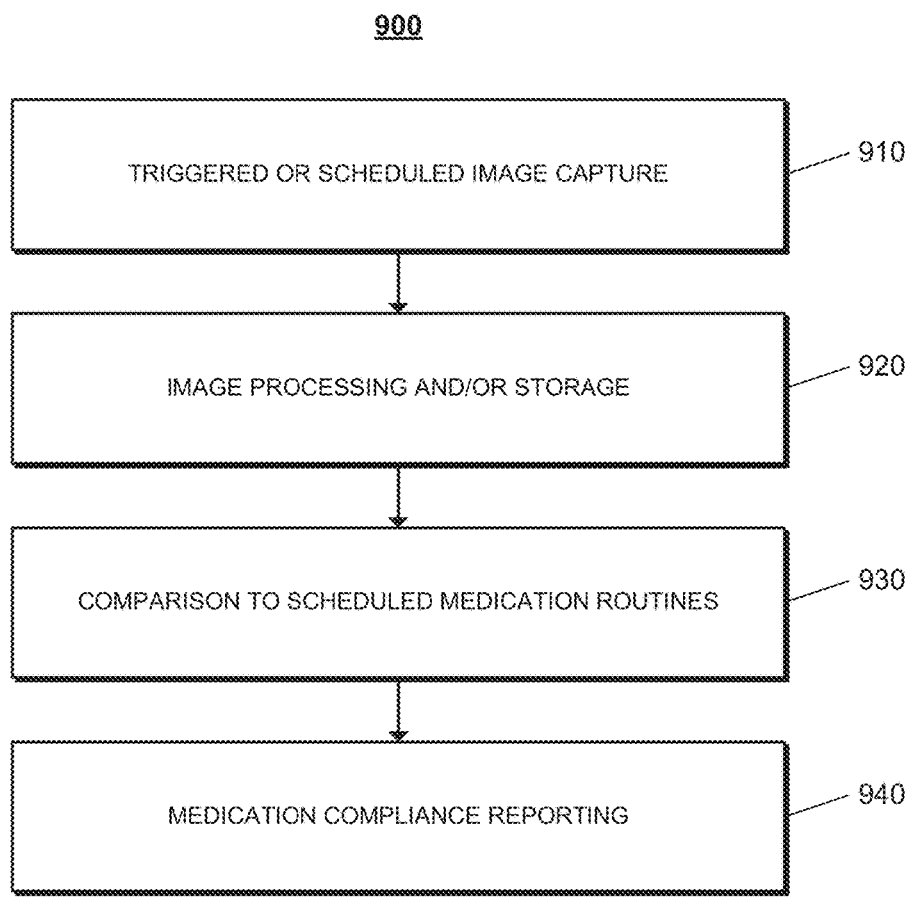

FIG. 9 illustrates an example process 900 for performing verification related to one or more medication events. The operations of the example process 900 are described generally as being performed by the system 300. The operations of the example process 900 may be performed by one of the components of the system 300 (e.g., the image sensing device 110, the gateway 120, the remote monitoring server 130, etc.) or may be performed by any combination of the components of the system 300. The operations of the example process 900 also may be performed by the system 500 or one or more components of the system 500. In some implementations, operations of the example process 900 may be performed by one or more processors included in one or more electronic devices.

In general, the process 900 produces a recorded history of medication consumption events for management and verification purposes. The process 900 also enables such events to be compared against known and pre-configured schedules or observed and profiled usage patterns so notifications can be generated for missed or improper medication times or consumption of improper medications. Features, which work in concert with the process 900, both guide and remind those taking medications through appropriate medication schedules to encourage overall medication adherence. Contextual information about the medication events can also be used to facilitate refills.

Figure 10:
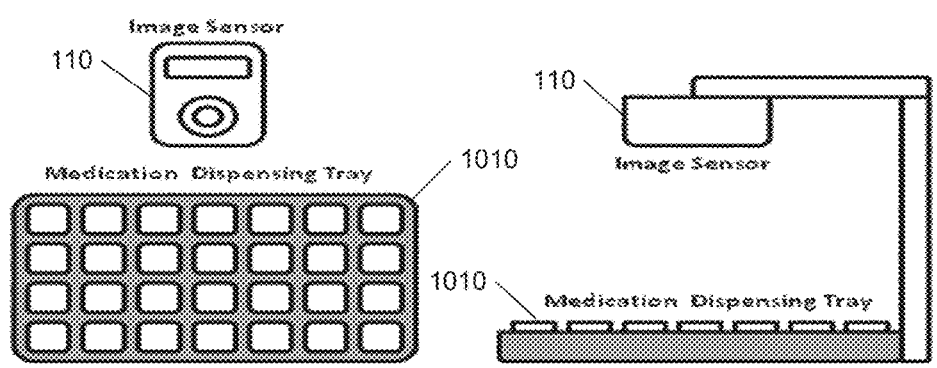

Medications are placed within close proximity to each other and to the image sensing device such that they are within the field of view of the device's camera and within sensing range of the device's or other sensors. Medications may be placed in a tray 1010 (as shown in the depiction of an example device in FIG. 10) or remain in native or other packaging within the sensed region. Medications in packaging can be distinguished on the basis of size, shape, color or other identifiable characteristics of the packaging, medication(s), or other added devices to promote differentiation.

The system 300 performs a triggered or scheduled image capture (910). For example, a medication event can be scheduled or signaled by one or more trigger sources. These sources include, but are not limited to: an optional medication presence sensing device (e.g., contact, capacitive, inductive, magnetic, RFID, or other sensor) or any combination of the image device's sensors (e.g., the image itself, passive infrared motion sensor, inertial sensor, etc.). The sources may include other sensors in a home or facility monitoring system to trigger image capture of a potential medication event. When an event is detected proximal to the medication(s) (e.g., motion detected near sensor), the image sensing device captures an image.

Following the image capture, the system 300 performs image processing and/or storage (920). The processing may be performed on the image sensing device, at the gateway, or on the remote monitoring servers to validate the accuracy of removed medications. For example, the image processing may be used to determine whether the exact medication(s) is removed from the correct locations in a medication dispensing tray. In this example, the system shown in FIG. 10 in both component and side view may be used. The system includes the image sensing device 110 and a medication dispensing tray 1010. As shown, the image sensing device 110 is oriented above the medication dispensing tray 1010. A field of view of the image sensing device 110 covers the entire medication dispensing tray 1010 and is close enough to the medication dispensing tray 1010 to image medications in the medication dispensing tray 1010 at a sufficient detail. Images of the medication dispensing tray 1010 may be analyzed to determine which, if any, medications (e.g., pills) from the medication dispensing tray 1010 have been removed and which, if any, medications (e.g., pills) remain in the medication dispensing tray 1010. Images of the medication dispensing tray 1010 may be taken based on a triggering event (e.g., a motion sensor of the image sensing device 110 indicating motion near the medication dispensing tray 1010, a contact sensor of the medication dispensing tray 1010 indicating medication has been removed, a contact sensor of a security system located on a door leading to a room in which the medication dispensing tray 1010 indicating that the door was been opened, etc.) or based on a timing schedule (e.g., image every four hours when the person is supposed to take medication).

After image processing, the system 300 performs a comparison to scheduled or expected medication routines (930). The removed medication(s) may be compared to preset scheduled medication routines to determine whether the quantity and type of medication(s) removed is consistent with a prescribed routine. Schedules can be pre-configured and entered by users. Expected events can be determined by comparing observed medication events to profiled user behavior.

Based on comparison results, the system 300 performs medication compliance reporting (940). For example, information about the medication removal event can be used to notify the individual taking the notification of improper medication removal (e.g., immediately). Also, if a scheduled event is not detected by any of the trigger sources within an acceptable and user-specified window of time, then a message can be generated to inform user(s) that a scheduled medication has been missed. Furthermore, data and images of the event or lack thereof can be forwarded to the gateway device 120 in the home or onto the remote monitoring servers 130 for storage or notification purposes. Users are able to retrieve historic data about medication consumption events stored in the system 300. From the remote monitoring servers 130, data and images can be sent to user devices 140 or a central monitoring station 150. Verification of medication events can be made by human inspection of images if desired. Medication management can be performed with or without image or other human-based verification mechanisms.

Referring again to FIG. 6, the system 300 performs profiling related to one or more medication events (640). Other passive sensors placed around the patient's location can be used to measure patient activity. Furthermore, user interface devices can be used to administer questionnaires or collect data from internal sensors (e.g., accelerometers, angular rate sensors, etc.). Data can be synthesized to derive aspects of behavior associated with fully compliant medication regimens. For example, user behavior can be analyzed during medication events to monitor compliance with related prerequisite activities (e.g., eating before or after a medication is consumed). Patient activity can also be analyzed to observe behaviors related to certain medications or related health indicators. For example, measurement of sleep, eating, or general activity level could be forwarded to the patient or caregivers to assess effects of medications. Third party data sources (e.g., pharmacy or clinician data) may be captured to augment existing data.

Figure 11:
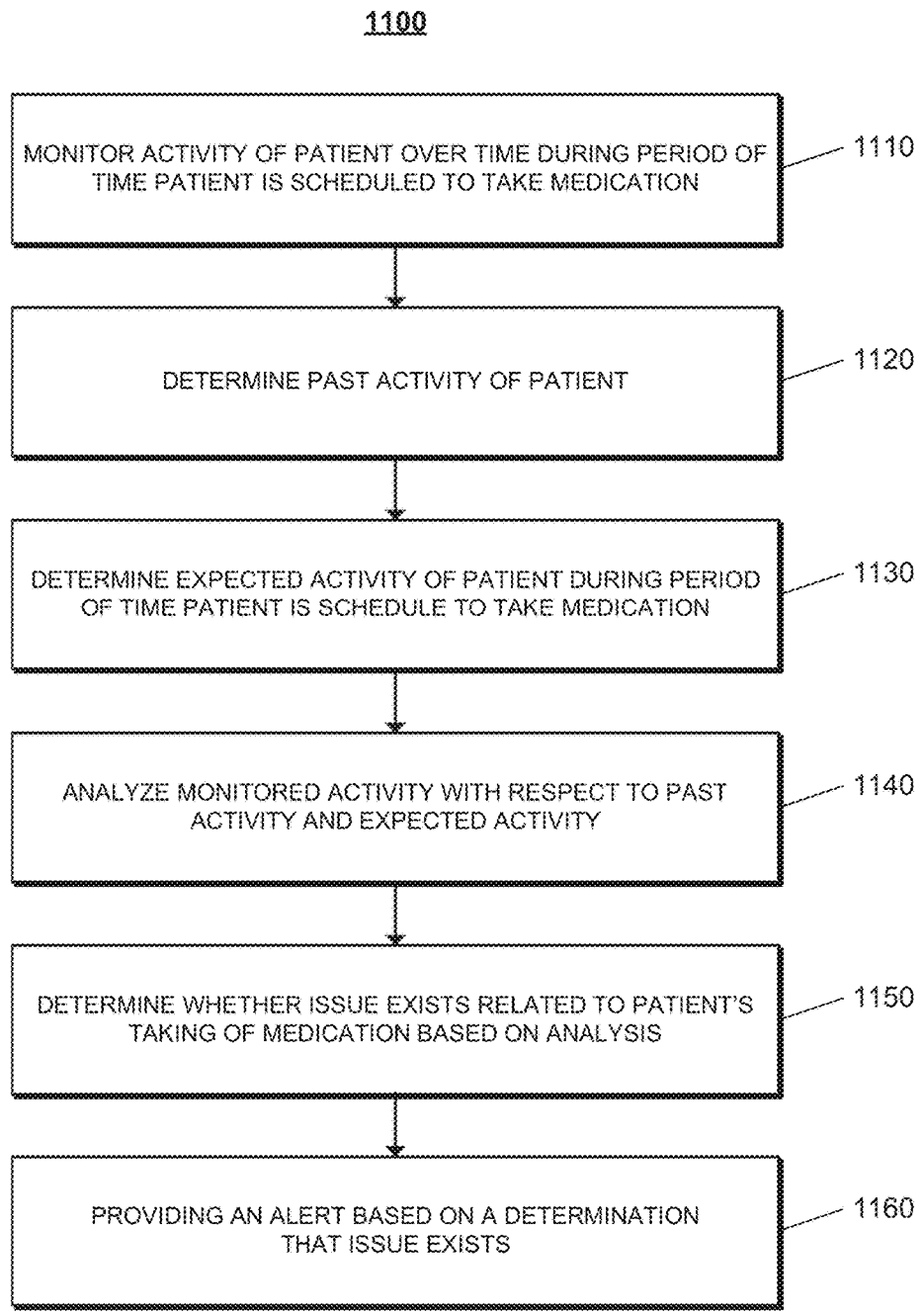

FIG. 11 illustrates an example process 1100 for performing profiling related to one or more medication events. The operations of the example process 1100 are described generally as being performed by the system 300. The operations of the example process 1100 may be performed by one of the components of the system 300 (e.g., the image sensing device 110, the gateway 120, the remote monitoring server 130, etc.) or may be performed by any combination of the components of the system 300. The operations of the example process 1100 also may be performed by the system 500 or one or more components of the system 500. In some implementations, operations of the example process 1100 may be performed by one or more processors included in one or more electronic devices.

The system 300 monitors activity of a patient over time during a period of time the patient is scheduled to take medication (1110). For example, the system 300 monitors activity of the patient within the patient's home. In this example, the system 300 may monitor any of the sensors described throughout this disclosure to monitor the patient's activity within the patient's home. The system 300 may consider any data collected by a monitoring system that monitors the patient's home with the data considered being any of the sensor data (e.g., contact sensor data, motion sensor data, image sensor data, bathroom usage data, medication consumption data, food consumption data, sleeping habits data, etc.) described throughout this disclosure. The system 300 may monitor activity of the patient over a relatively long period of time during which the patient is scheduled to take the medication (e.g., over a number of days, weeks, months, or years).

The system 300 determines past activity of patient (1120). For instance, the system 300 determines past activity of the patient within the patient's home based on monitoring the patient's activity over time. In some examples, the past activity of the patient is activity of the patient that occurred before the patient began taking the medication. In these examples, the past activity of the patient serves as a baseline by which the monitored activity may be compared against. In addition, the past activity of the patient may be activity of the patient that occurred after the patient began taking the medication, but prior to the monitored activity. In this case, the past activity of the patient serves as a baseline of the patient's activity while taking the medication and may be compared against the current monitored activity to determine whether the patient's activity has changed (e.g., because the patient has stopped taking the medication).

The system 300 determines expected activity of the patient during the period of time the patient is schedule to take medication (1130). For instance, the system 300 may access one or more behavior profiles that describe how the patient is expected to act during the period of time the patient is scheduled to take medication. The one or more behavior profiles may indicate that the patient should see a decrease in bathroom visits when taking the medication or that the sleeping habits of the patient should stabilize when taking the medication.

The system 300 analyzes the monitored activity with respect to the past activity and the expected activity (1140). For instance, the system 300 compares the current monitored activity of the patient with the past activity of the patient to see if activity of the patient has changed. In addition, the system 300 may compare the current monitored activity of the patient with the expected activity to determine whether the current monitored activity of the patient matches the expected activity. When the expected activity relates to a change in the patient's activity, the system 300 evaluates the change in the patient's activity that is expected with respect to a result of a comparison of the current monitored activity of the patient with the past activity of the patient.

The system 300 determines whether an issue exists related to the patient's taking of medication based on the analysis (1150). For example, the system 300 evaluates a comparison of the current monitored activity of the patient with the past activity of the patient and determines whether the activity of the patient has changed. In this example, the system 300 determines whether the patient's activity is expected to change when taking the medication and, if so, how the patient's activity is expected to change. When the patient's activity is expected to change and the system 300 determines that the patient's activity has not changed, the system 300 determines that the patient's medication is not working or that the patient is not taking the medication. When the system 300 determines that the patient's activity has changed in a manner that is not expected, the system 300 may determine that the patient is suffering from one or more side effects of taking the medication.

In some examples, the system 300 evaluates a comparison of the current monitored activity of the patient with the expected activity of the patient and determines whether the current monitored activity of the patient matches the expected activity of the patient. In these examples, the system 300 determines that the patient's medication is not working or that the patient is not taking the medication based on determining that the current monitored activity of the patient does not match the expected activity of the patient. When the system 300 determines that the current monitored activity of the patient matches the expected activity of the patient, the system 300 determines that the medication is working and monitors for other changes in activity that would suggest a potential side effect of the medication.

The system 300 provides an alert based on a determination that an issue exists related to the patient's taking of medication (1160). For example, the system 300 provides an alert to the patient's doctor, the patient's caregiver, or a remote monitoring station. In this example, the system 300 may provide an alert to a remote device (e.g., mobile phone) of the patient's doctor, the patient's caregiver, or a remote monitoring station to alert the patient's doctor, the patient's caregiver, or the remote monitoring station to the issue related to the patient's taking of the medication.

FIG. 12 illustrates example alert interfaces. For example, a first alert interface 1210 provides an alert that a patient's sleep habits indicate that the patient is not taking his or her anti-depressant medication. In this example, the system 300 monitors sleep habits of a patient that takes anti-depressant medication using a bed sensor (e.g., a bed mat) that senses movement (e.g., restlessness) of a person lying down in a bed. The system 300 also may monitor one or more motion or contact sensors that measure activity of the patient during hours in which the patient should be sleeping. Based on monitoring the sleep habits of the patient, the system 300 determines that the patient is having trouble sleeping and that the sleep habits of the patient are erratic. Because sleep habits stabilize for patients when properly taking anti-depressant medication, the system 300 determines that the sleep habits for the patient indicate that the patient is not taking his or her anti-depressant medication. The system 300 sends the alert that causes display of the first alert interface 1210 based on the determination that the sleep habits for the patient indicate that the patient is not taking his or her anti-depressant medication.

The first alert interface 1210 provides several user input controls that help a recipient of the alert (e.g., a doctor, a caregiver, etc.) evaluate and handle the alert. For instance, the first alert interface 1210 includes a contact patient interface control 1211 that allows the recipient of the alert to contact the patient in response to selecting the contact patient interface control 1211. The contact patient interface control 1211 may initiate a telephone call to the patient, may initiate an email to the patient, may initiate an instant messaging session with the patient, or may initiate any other type of communication session with the patient that enables discussion of the situation.

The first alert interface 1210 also includes a view records input control 1212 that enables a recipient of the alert (e.g., a doctor, a caregiver, etc.) to receive information regarding the records of the patient. For instance, the recipient of the alert may select the view records input control 1212 and, based on the selection, the system 300 retrieves the medical records of the patient from a remote database and displays the retrieved medical records to the recipient of the alert. The recipient of the alert reviews the records of the patient and makes a determination of how to handle the alert. In some implementations, the system 300 may require the recipient of the alert to provide identification information (e.g., a user name and a password) that verifies that the recipient of the alert is authorized to view the medical records of the patient prior to allowing the recipient of the alert to view the medical records.

The first alert interface 1210 further includes an increase monitoring input control 1213 that enables a recipient of the alert (e.g., a doctor, a caregiver, etc.) to cause an increase in the monitoring procedures used to verify whether the patient is properly taking his or her anti-depressant medication. Because the patient is expected to be failing to comply with his or her medication schedule, the recipient of the alert may determine that increased monitoring of the patient's medication schedule would be beneficial to confirm whether or not the patient is failing to comply with his or her medication schedule. For example, the increase monitoring input control 1213 may cause the system 300 to increase automated monitoring for whether the patient is complying with the medication schedule. In this example, the system 300 may increase the frequency with which the system 300 takes images of the patient's medication to get a more accurate timing of when medication is being removed from the patient's medication tray or other container.

In addition, the system 300 may add additional monitoring procedures based on receiving user input selecting the increase monitoring input control 1213. For example, prior to receiving user input selecting the increase monitoring input control 1213, the system 300 may monitor images of the patient's medication, but may not be monitoring images of the patient taking the medication. In this example, in response to receiving user input selecting the increase monitoring input control 1213, the system 300 begins capturing images of the patient taking the medication and analyzes the captured images to verify that the patient is actually taking the medication when it is removed from the medication tray or other container and to verify that the person taking the medication is in fact the patient (e.g., using facial recognition or other biometric identification technology).

Further, the system 300 may require additional manual monitoring for whether the patient is complying with the medication schedule in response to receiving user input selecting the increase monitoring input control 1213. For instance, the system 300 may schedule in home monitoring visits by a caregiver at scheduled medication times, so that the caregiver can verify that the patient is taking his or her medication at the scheduled medication times. The system 300 also may begin requiring the patient to provide user input confirming that medication events have occurred. The system 300 may use the required user input as an additional data point in verifying medication compliance and sending reminders or alerts.

The second alert interface 1220 provides an alert that bathroom habits indicate that a medication that a patient is taking for a urinary tract infection is not working. For instance, the system 300 monitors bathroom habits of the patient using a toilet sensor that tracks usage of the toilet (e.g., a sensor that tracks when a toilet is flushed). The system 300 also may monitor one or more motion or contact sensors that measure activity of the patient entering and/or leaving the bathroom. Based on monitoring the bathroom habits of the patient, the system 300 determines that the patient is frequently using the bathroom at a rate that is higher than a past baseline established for the patient and consistent with a rate at which the patient was using the bathroom after contracting the urinary tract infection, but prior to starting the medication. Because bathroom usage decreases for patients when medication is properly combatting a urinary tract infection, the system 300 determines that the bathroom habits for the patient indicate that the medication that the patient is taking for the urinary tract infection is not working. The system 300 sends the alert that causes display of the second alert interface 1220 based on the determination that the medication that the patient is taking for the urinary tract infection is not working.

The second alert interface 1220 provides several user input controls that help a recipient of the alert (e.g., a doctor, a caregiver, etc.) evaluate and handle the alert. For instance, the second alert interface 1220 includes a prescribe new medication input control 1221 that allows the recipient of the alert to prescribe a new medication for the patient. In response to receiving user input selecting the prescribe new medication input control 1221, the system 300 displays an interface that allows the recipient of the alert to select a new medication and a dosage for the new medication. In response to receiving input selecting the new medication and the dosage for the new medication, the system 300 automatically sends a prescription for the new medication to a pharmacy registered for the patient and provides the patient or the patient's caregiver with a message indicating that the patient's doctor has prescribed a new medication for the patient, that the new medication is available at the pharmacy registered for the patient, and that use of the old medication should be discontinued. In some implementations, the system 300 may require the recipient of the alert to provide identification information (e.g., a user name and a password) that verifies that the recipient of the alert is the patient's doctor prior to allowing the recipient of the alert to prescribe a new medication for the patient.

The second alert interface 1220 also includes a change dosage input control 1222 that allows the recipient of the alert to change a dosage at which the patient is currently taking the medication. In response to receiving user input selecting the change dosage input control 1222, the system 300 displays an interface that allows the recipient of the alert to select a new dosage for the medication. In response to receiving input selecting the new dosage, the system 300 automatically provides the patient or the patient's caregiver with a message indicating that the patient's doctor has set a new dosage for the medication the patient is taking for the urinary tract infection and the patient should begin taking the new dosage. The system 300 may begin verifying that the patient is taking the new dosage based on the setting of the new dosage. In some implementations, the system 300 may require the recipient of the alert to provide identification information (e.g., a user name and a password) that verifies that the recipient of the alert is the patient's doctor prior to allowing the recipient of the alert to change the dosage for the patient's medication.

The second alert interface 1220 further includes a view records input control 1223 that enables a recipient of the alert (e.g., a doctor, a caregiver, etc.) to receive information regarding the records of the patient. For instance, the recipient of the alert may select the view records input control 1223 and, based on the selection, the system 300 retrieves the medical records of the patient from a remote database and displays the retrieved medical records to the recipient of the alert. The recipient of the alert reviews the records of the patient and makes a determination of how to handle the alert. In some implementations, the system 300 may require the recipient of the alert to provide identification information (e.g., a user name and a password) that verifies that the recipient of the alert is authorized to view the medical records of the patient prior to allowing the recipient of the alert to view the medical records.

In addition, the second alert interface 1220 includes a contact patient interface control 1224 that allows the recipient of the alert to contact the patient in response to selecting the contact patient interface control 1224. The contact patient interface control 1224 may initiate a telephone call to the patient, may initiate an email to the patient, may initiate an instant messaging session with the patient, or may initiate any other type of communication session with the patient that enables discussion of the situation.

The third alert interface 1230 provides an alert that an increase in pain reliever consumption by a patient indicates that headaches are a side effect of a new medication for the patient. For instance, the system 300 monitors consumption of pain relievers by the patient using any of the techniques described throughout this disclosure for monitoring medication usage. Based on monitoring the consumption of pain relievers by the patient, the system 300 determines that the patient is frequently taking pain relievers at a rate that is higher than a past baseline established for the patient prior to starting the new medication. Because pain reliever consumption increases for patients when medication is causing headaches as a side effect, the system 300 determines that headaches are a side effect of the new medication for the patient. The system 300 sends the alert that causes display of the third alert interface 1230 based on the determination that headaches are a side effect of the new medication for the patient.

The third alert interface 1230 provides several user input controls that help a recipient of the alert (e.g., a doctor, a caregiver, etc.) evaluate and handle the alert. For instance, the third alert interface 1230 includes a prescribe new medication input control 1231 that allows the recipient of the alert to prescribe a new medication for the patient. In response to receiving user input selecting the prescribe new medication input control 1231, the system 300 displays an interface that allows the recipient of the alert to select a new medication and a dosage for the new medication. In response to receiving input selecting the new medication and the dosage for the new medication, the system 300 automatically sends a prescription for the new medication to a pharmacy registered for the patient and provides the patient or the patient's caregiver with a message indicating that the patient's doctor has prescribed a new medication for the patient, that the new medication is available at the pharmacy registered for the patient, and that use of the old medication should be discontinued. In some implementations, the system 300 may require the recipient of the alert to provide identification information (e.g., a user name and a password) that verifies that the recipient of the alert is the patient's doctor prior to allowing the recipient of the alert to prescribe a new medication for the patient.

The third alert interface 1230 also includes a change dosage input control 1232 that allows the recipient of the alert to change a dosage at which the patient is currently taking the medication. In response to receiving user input selecting the change dosage input control 1232, the system 300 displays an interface that allows the recipient of the alert to select a new dosage for the medication. In response to receiving input selecting the new dosage, the system 300 automatically provides the patient or the patient's caregiver with a message indicating that the patient's doctor has set a new dosage for the medication and the patient should begin taking the new dosage. The system 300 may begin verifying that the patient is taking the new dosage based on the setting of the new dosage. In some implementations, the system 300 may require the recipient of the alert to provide identification information (e.g., a user name and a password) that verifies that the recipient of the alert is the patient's doctor prior to allowing the recipient of the alert to change the dosage for the patient's medication.

The third alert interface 1230 further includes a view records input control 1233 that enables a recipient of the alert (e.g., a doctor, a caregiver, etc.) to receive information regarding the records of the patient. For instance, the recipient of the alert may select the view records input control 1233 and, based on the selection, the system 300 retrieves the medical records of the patient from a remote database and displays the retrieved medical records to the recipient of the alert. The recipient of the alert reviews the records of the patient and makes a determination of how to handle the alert. In some implementations, the system 300 may require the recipient of the alert to provide identification information (e.g., a user name and a password) that verifies that the recipient of the alert is authorized to view the medical records of the patient prior to allowing the recipient of the alert to view the medical records.

In addition, the third alert interface 1230 includes a contact patient interface control 1234 that allows the recipient of the alert to contact the patient in response to selecting the contact patient interface control 1234. The contact patient interface control 1234 may initiate a telephone call to the patient, may initiate an email to the patient, may initiate an instant messaging session with the patient, or may initiate any other type of communication session with the patient that enables discussion of the situation.

Referring again to FIG. 6, the system 300 performs reporting related to one or more medication events (650). Data (including images) from sensors, trigger sources, user interface devices, monitoring centers can be securely stored on the remote servers or immediately forwarded to the patient, caregivers, or monitoring center. The remote servers, monitoring center, or user interface device can initiate communication to the patient, caregivers, or other trusted parties. Communication can take the form of email, text message, automated or human telephone call, push notification, or other user interface mechanism. Communication can be established based on rules established by the patient, caregivers, monitoring center, or set by default. Rules can be applied to raw or processed data and initiate preemptive action (e.g., reminders) or post medication event action. Processing can also be used to score patients on their compliance level. Scores can be compared to patient historic data or various population scores.

Information can also be requested by users. For example, a patient can request information about a particular medication or medication regimen through interaction with a user interface device or access to stored records on remote servers (e.g., via a secure website). For example, a patient's user interface device (e.g., mobile device with mobile application) could identify a medication (via user selection, imaging, or wireless tag) and provide more information about the medication, medication routine, compliance with and behaviors associated with that routine.

Also, information assessed from the analysis of medication reporting data can be used to remind users to refill medications or to signal third-parties (e.g., pharmacies, home care agents, caregivers, etc.) of the need for refills or to initiate refills. Contextual data can also be combined with other sensed data to make health or wellness assessments based on perceived compliance level and user activity.

Figure 13:
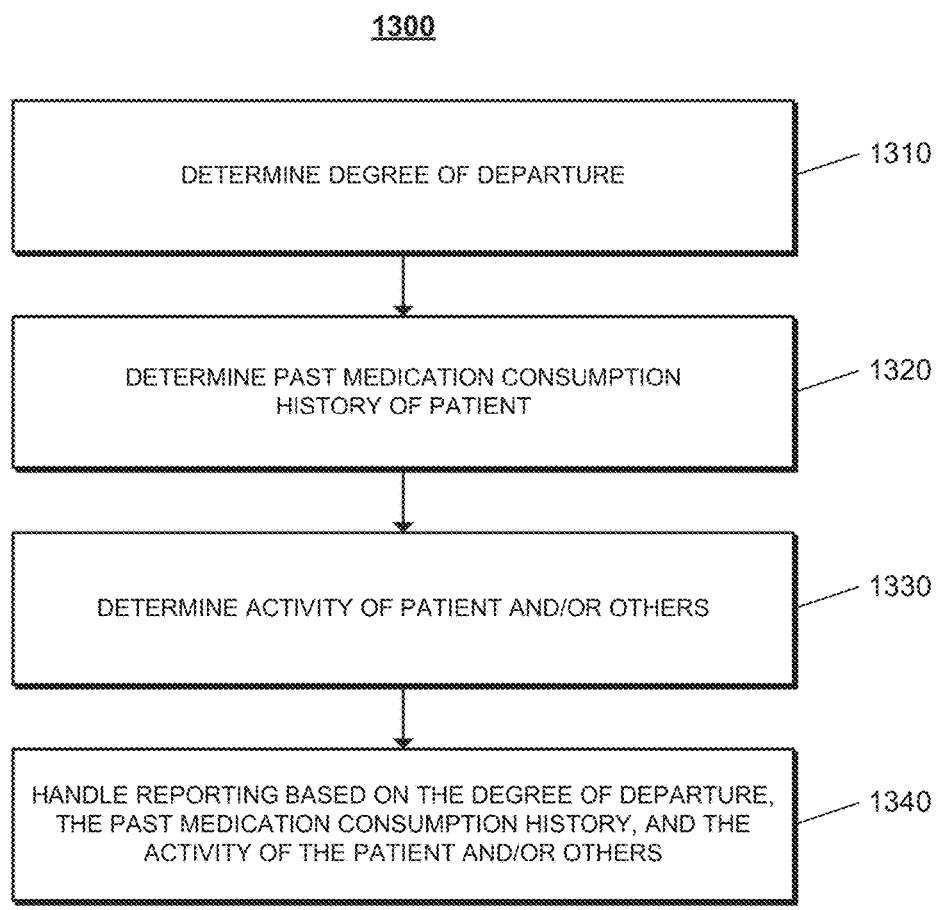

FIG. 13 illustrates an example process 1300 for performing reporting related to one or more medication events. The operations of the example process 1300 are described generally as being performed by the system 300. The operations of the example process 1300 may be performed by one of the components of the system 300 (e.g., the image sensing device 110, the gateway 120, the remote monitoring server 130, etc.) or may be performed by any combination of the components of the system 300. The operations of the example process 1300 also may be performed by the system 500 or one or more components of the system 500. In some implementations, operations of the example process 1300 may be performed by one or more processors included in one or more electronic devices.

The system 300 determines a degree of departure by a patient from a schedule of medication events (1310). For instance, the system 300 evaluates how much the patient has departed from the schedule of medication events. The degree of departure may be determined in terms of time, amount of medication, and combination of medications taken. For example, the system 300 may determine how late the patient is in taking the medication or how early the patient was in taking the medication and determine a degree of departure based on how late the patient is in taking the medication or how early the patient was in taking the medication.

In some implementations, the system 300 may determine a dosage of medication taken by the patient and compare the dosage of medication taken by the patient with the dosage the patient was supposed to take. In these implementations, the system 300 computes a difference between the dosage taken and the dosage scheduled (e.g., too much or too little) and determines a degree of departure based on the difference between the dosage taken and the dosage scheduled.

In some examples, the system 300 may determine a combination of medications taken by the patient and compare the combination of medications taken by the patient with the combination of medications the patient was supposed to take. In these examples, the system 300 computes a difference between the combination of medications taken and the combination of medications scheduled and determines a degree of departure based on the difference between the combination of medications taken and the combination of medications scheduled. The system 300 also may evaluate the combination of medications taken against a reference table of potentially dangerous combinations of medications and determine a degree of departure based on the evaluation.

The system 300 determines past medication consumption history of the patient (1320). For example, the system 300 monitors, over time, how closely the patient has followed a schedule of medication events in the past. In this example, the system 300 determines, based on the monitoring, whether the patient strictly follows the schedule of medication events, generally follows the schedule of medication events, or consistently fails to follow the schedule of medication events.

The system 300 determines activity of the patient and/or others (1330). For example, the system 300 monitors activity of the patient and/or others within the patient's home. In this example, the system 300 may monitor any of the sensors described throughout this disclosure to monitor the activity within the patient's home. The system 300 may consider any data collected by a monitoring system that monitors the patient's home with the data considered being any of the sensor data (e.g., contact sensor data, motion sensor data, image sensor data, etc.) described throughout this disclosure.

In addition, the system 300 monitors activity of the patient and/or others outside of the patient's home. For instance, the system 300 may receive reports from a mobile device (e.g., mobile phone) of the patient or the patient's caregiver that indicate a location of the mobile device determined using Global Positioning System (GPS) technology. The system 300 also may monitor activity of the patient or the patient's caregiver outside of the patient's home using any other type of tracking device that is capable of tracking the location of the patient or the patient's caregiver outside of the patient's home.

The system 300 handles reporting based on the degree of departure, the past medication consumption history, and the activity of the patient and/or others (1340). In this regard, the system 300 performs a tiered alerting process that is used to determine a destination of the alert (or type of alert) based on the degree of departure, the past medication consumption history, and/or the activity of the patient and/or others. For example, the system 300 may provide in home alerts or remote alerts depending on the degree of departure, the past medication consumption history, and the activity of the patient and/or others. In this example, the system 300 may first provide an in home alert when the degree of departure is relatively low, the patient frequently misses medication events, and activity is detected within the patient's home. If the medication event is not completed within a threshold period of time after providing the in home alert, the system 300 may elevate the situation and provide an alert to a remote caregiver or monitoring station. When the system 300 determines that the degree of departure is relatively serious, the patient has strictly complied with the schedule medication events in the past, and activity is not detected within the patient's home, the system 300 may forego the in home alert and immediately provide an alert to a remote caregiver or monitoring station given the circumstances. By tailoring the reporting or alerting response to a missed medication event, the system 300 provides a flexible solution that is consistent with the circumstances of the situation surrounding the missed medication event.

FIG. 14 illustrates an example data structure 1400 used in providing alerts. The system 300 consults the data structure 1400 in determining a destination of an alert and what type of alert to provide. As shown, the data structure 1400 includes a first column 1410 for activity within the home, a second column 1420 for a degree of departure, a third column 1430 for past consumption history, and a fourth column 1440 that defines the type of alert to provide. In using the data structure 1400, the system 300 determines whether activity exists in a patient's home, determines a degree of departure of the missed medication event, determines past consumption history for the patient, and compares the determined activity in the patient's home, the degree of departure, and the past consumption history for the patient against the data stored in the columns 1410, 1420, and 1430. Based on the comparison, the system 300 detects a match between the circumstances of the missed medication event and the data in the columns 1410, 1420, and 1430 and provides the type of alert defined in the column 1440 for the matching record.

As shown, the first row in the data structure defines that the system 300 provides only an in home alert when the system 300 detects activity in the patient's home, the degree of departure is low, and the patient's past consumption history is poor. The second row in the data structure defines that the system 300 immediately provides an alert to a remote caregiver when the system 300 does not detect activity in the patient's home, the degree of departure is moderate, and the patient's past consumption history is strict. The third row in the data structure defines that the system 300 immediately provides an alert to emergency services, an alert to a remote caregiver, and an in home alert when the system 300 detects activity in the patient's home, the degree of departure is potentially lethal, and the patient's past consumption history is average. Because the degree of departure is potentially lethal (e.g., the patient has taken a potentially lethal combination of medication or a potentially lethal dosage of a medication), the system 300 immediately provides several alerts.

The data structure 1400 includes three rows for brevity and ease of explanation. Actual implementations may include more (perhaps many more) or fewer rows. Any combinations of potential values for the activity of the patient and others, the degree of departure, and the patient's past consumption history may be used to trigger any types of alerts per the preferences of the patient, the patient's caregiver, the patient's family, the patient's doctor, or any other person that handles medication monitoring for the patient.

The described systems, methods, and techniques may be implemented in digital electronic circuitry, computer hardware, firmware, software, or in combinations of these elements. Apparatus implementing these techniques may include appropriate input and output devices, a computer processor, and a computer program product tangibly embodied in a machine-readable storage device for execution by a programmable processor. A process implementing these techniques may be performed by a programmable processor executing a program of instructions to perform desired functions by operating on input data and generating appropriate output. The techniques may be implemented in one or more computer programs that are executable on a programmable system including at least one programmable processor coupled to receive data and instructions from, and to transmit data and instructions to, a data storage system, at least one input device, and at least one output device. Each computer program may be implemented in a high-level procedural or object-oriented programming language, or in assembly or machine language if desired and in any case, the language may be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of non-volatile memory, including by way of example semiconductor memory devices, such as Erasable Programmable Read-Only Memory (EPROM), Electrically Erasable Programmable Read-Only Memory (EEPROM), and flash memory devices; magnetic disks such as internal hard disks and removable disks; magneto-optical disks; and Compact Disc Read-Only Memory (CD-ROM). Any of the foregoing may be supplemented by, or incorporated in, specially-designed ASICs (application-specific integrated circuits).

It will be understood that various modifications may be made. For example, other useful implementations could be achieved if steps of the disclosed techniques were performed in a different order and/or if components in the disclosed systems were combined in a different manner and/or replaced or supplemented by other components. Accordingly, other implementations are within the scope of the disclosure.

What is claimed is:

1. A system comprising:
   at least one processor; and
   at least one memory coupled to the at least one processor having stored thereon instructions which, when executed by the at least one processor, causes the at least one processor to perform operations comprising:
   detecting a departure by a patient from a schedule of medication consumption events based on output from at least one sensor within a property in which the patient is located;
   based on the detection of the departure by the patient from the schedule of medication consumption events:
   determining a dosage of medication taken by the patient,
   comparing the dosage of medication taken by the patient with a reference table that comprises a list of potentially dangerous combinations of medications,
   computing a difference between the dosage of medication taken by the patient and the list of potentially dangerous combinations of medications,
   determining a degree of departure by the patient from the schedule of medication consumption events based on the difference between the dosage of medication taken by the patient and the list of potentially dangerous combinations of medications,
   determining past medication consumption history of the patient, and
   determining activity of at least one of the patient or another person associated with the patient that indicates a proximity of at least one of the patient or another person associated with the patient to a medication in the property required for the patient to consume based on the schedule of medication consumption events; and
   handling reporting of the detection of the departure by the patient based on the determined degree of departure, the determined past medication consumption history, and the determined activity of at least one of the patient or another person associated with the patient.

2. The system of claim 1, wherein determining the degree of departure by the patient from the schedule of medication consumption events comprises evaluating how much the patient has departed from the schedule of medication consumption events.

3. The system of claim 1, wherein determining the degree of departure by the patient from the schedule of medication consumption events comprises determining the degree of departure in terms of at least one of an amount of time associated with the departure, an amount of medication associated with the departure, or a combination of medications taken in the departure.

4. The system of claim 3, wherein determining the degree of departure in terms of at least one of an amount of time associated with the departure, an amount of medication associated with the departure, or a combination of medications taken in the departure comprises determining the degree of departure in terms of an amount of time associated with the departure.

5. The system of claim 4, wherein determining the degree of departure in terms of an amount of time associated with the departure comprises:
   determining how late the patient is in taking the dosage of medication or how early the patient was in taking the dosage of medication; and
   determining a degree of departure based on how late the patient is in taking the dosage of medication or how early the patient was in taking the dosage of medication.

6. The system of claim 3, wherein determining the degree of departure in terms of at least one of an amount of time associated with the departure, an amount of medication associated with the departure, or a combination of medications taken in the departure comprises determining the degree of departure in terms of an amount of medication associated with the departure.

7. The system of claim 6, wherein determining the degree of departure in terms of the amount of medication associated with the departure comprises:
   comparing the dosage of medication taken by the patient with the dosage of medication the patient was scheduled to take;
   computing a difference between the dosage of medication taken by the patient and the dosage of medication the patient was scheduled to take; and
   determining a degree of departure based on the difference between the dosage of medication taken by the patient and the dosage of medication the patient was scheduled to take.

8. The system of claim 3, wherein determining the degree of departure in terms of at least one of an amount of time associated with the departure, an amount of medication associated with the departure, or a combination of medications taken in the departure comprises determining the degree of departure in terms of a combination of medications taken in the departure.

9. The system of claim 8, wherein determining the degree of departure in terms of the combination of medications taken in the departure comprises:
   determining a combination of medications taken by the patient;
   comparing the combination of medications taken by the patient with a combination of medications the patient was scheduled to take;
   identifying a difference between the combination of medications taken by the patient and the combination of medications the patient was scheduled to take; and
   determining a degree of departure based on the difference between the combination of medications taken by the patient and the combination of medications the patient was scheduled to take.

10. The system of claim 1, wherein determining past medication consumption history of the patient comprises monitoring, over time, how closely the patient has followed a schedule of medication consumption events in the past and determining, based on the monitoring, whether the patient strictly follows the schedule of medication consumption events, generally follows the schedule of medication consumption events, or consistently fails to follow the schedule of medication consumption events.

11. The system of claim 1, wherein determining activity of at least one of the patient or another person associated with the patient comprises determining activity of another person associated with the patient.

12. The system of claim 1, wherein determining activity of at least one of the patient or another person associated with the patient comprises determining activity of the patient and another person associated with the patient.

13. The system of claim 1, wherein determining activity of at least one of the patient or another person associated with the patient comprises monitoring, based on sensor data from at least one sensor within the property in which the patient is located, activity of at least one of the patient or another person associated with the patient within the property.

14. The system of claim 1, wherein determining activity of at least one of the patient or another person associated with the patient comprises monitoring activity of at least one of the patient or another person associated with the patient outside of the property.

15. The system of claim 1, wherein handling reporting of the detection of the departure by the patient comprises performing a tiered alerting process that is used to determine a destination or type of an alert based on the determined degree of departure, the determined past medication consumption history, and the determined activity of at least one of the patient or another person associated with the patient.

16. The system of claim 15, wherein performing the tiered alerting process that is used to determine the destination or type of the alert comprises providing one or more in-property or remote alerts depending on the determined degree of departure, the determined past medication consumption history, and the determined activity of at least one of the patient or another person associated with the patient.

17. The system of claim 16, wherein providing one or more in-property or remote alerts depending on the determined degree of departure, the determined past medication consumption history, and the determined activity of at least one of the patient or another person associated with the patient comprises initially providing an in-property alert based on the degree of departure being relatively low, the patient frequently missing medication consumption events, and activity being detected within the property.

18. The system of claim 17, wherein providing one or more in-property or remote alerts depending on the determined degree of departure, the determined past medication consumption history, and the determined activity of at least one of the patient or another person associated with the patient comprises:
   determining that a medication consumption event in the schedule of medication consumption events has not been completed within a threshold period of time after providing the in-property alert; and
   based on the determination that the medication consumption event in the schedule of medication consumption events has not been completed within the threshold period of time after providing the in-property alert, providing a remote alert to a remote caregiver or monitoring station.

19. The system of claim 16, wherein providing one or more in-property or remote alerts depending on the determined degree of departure, the determined past medication consumption history, and the determined activity of at least one of the patient or another person associated with the patient comprises foregoing an in-property alert and immediately providing a remote alert to a remote caregiver or monitoring station based on the degree of departure being relatively serious, the patient having strictly complied with the schedule of medication consumption events in the past, and a lack of activity being detected within the property.

* * * * *